(12) United States Patent
Docktor et al.

(10) Patent No.: US 12,308,099 B2
(45) Date of Patent: May 20, 2025

(54) EXTENDED REALITY MEDICAL REPORT GENERATING SYSTEM

(71) Applicants: Children's Medical Center Corporation, Boston, MA (US); Klick Inc., Ontario (CA)

(72) Inventors: Michael J. Docktor, Boston, MA (US); Kate Donovan, Boston, MA (US); Yan Fossat, Ontario (CA); John S. Brownstein, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 900 days.

(21) Appl. No.: 17/002,221

(22) Filed: Aug. 25, 2020

(65) Prior Publication Data

US 2020/0388363 A1 Dec. 10, 2020

Related U.S. Application Data

(63) Continuation of application No. PCT/US2019/019598, filed on Feb. 26, 2019.

(60) Provisional application No. 62/635,355, filed on Feb. 26, 2018.

(51) Int. Cl.
| | |
|---|---|
| *G16H 15/00* | (2018.01) |
| *G06F 21/62* | (2013.01) |
| *G06T 11/00* | (2006.01) |
| *G09B 23/28* | (2006.01) |
| *G09B 23/30* | (2006.01) |
| *G16H 10/60* | (2018.01) |
| *G16H 50/50* | (2018.01) |

(52) U.S. Cl.
CPC ......... *G16H 15/00* (2018.01); *G06F 21/6245* (2013.01); *G06T 11/00* (2013.01); *G09B 23/28* (2013.01); *G09B 23/30* (2013.01); *G16H 10/60* (2018.01); *G16H 50/50* (2018.01); *G06T 2210/41* (2013.01)

(58) Field of Classification Search
None
See application file for complete search history.

(56) References Cited

U.S. PATENT DOCUMENTS

| | | | |
|---|---|---|---|
| 2010/0257214 A1* | 10/2010 | Bessette | G16H 10/60 707/812 |
| 2010/0305928 A1 | 12/2010 | Cohen et al. | |

(Continued)

OTHER PUBLICATIONS

International Search Report and Written Opinion for corresponding PCT Patent Applicaiton No. PCT/US19/19598 mailed Apr. 30, 2019 (12 pages).

*Primary Examiner* — James B Hull
(74) *Attorney, Agent, or Firm* — Greenberg Traurig, LLP; Melissa Hunter-Ensor; Kristopher Reichlen

(57) ABSTRACT

Embodiments described herein provide a method and apparatus for creating a representative medical report customized for a specific patient. The method retrieves medical findings for the patient and allows a doctor or user to enter those findings into a virtual realization screen. The virtual realization screen allows the doctor to pin localized conditions to the locations on the specific patient where the condition occurs. Diffuse conditions are painted onto affected segments. Multiple segments of a patient's body or body system may be jointed together so that the patient is teleported through their specific medical report.

19 Claims, 21 Drawing Sheets

(56) References Cited

U.S. PATENT DOCUMENTS

2013/0054271 A1* 2/2013 Langford ............... G16H 10/60
705/3
2020/0293174 A1* 9/2020 Diaz ...................... A61B 34/25

* cited by examiner

| Location | Base | Loss of Vascularity | Anastomosis Fwd | Anastomosis Rev | Erythema | Granularity | Ulceration | Type ID |
|---|---|---|---|---|---|---|---|---|
| esoph | 1 | 0/1 | 0/1 | 0/1 | 0/1 | 0/1 | 0/1 | tm/nm |
| stoma | 1 | 0/1 | 0/1 | 0/1 | 0/1 | 0/1 | 0/1 | tm/nm |
| duode | 1 | 0/1 | 0/1 | 0/1 | 0/1 | 0/1 | 0/1 | tm/nm |
| cecum | 1 | 0/1 | 0/1 | 0/1 | 0/1 | 0/1 | 0/1 | tm/nm |
| ascen | 1 | 0/1 | 0/1 | 0/1 | 0/1 | 0/1 | 0/1 | tm/nm |
| trans | 1 | 0/1 | 0/1 | 0/1 | 0/1 | 0/1 | 0/1 | tm/nm |
| desce | 1 | 0/1 | 0/1 | 0/1 | 0/1 | 0/1 | 0/1 | tm/nm |
| sigmo | 1 | 0/1 | 0/1 | 0/1 | 0/1 | 0/1 | 0/1 | tm/nm |
| rectu | 1 | 0/1 | 0/1 | 0/1 | 0/1 | 0/1 | 0/1 | tm/nm |
| ileum | 1 | 0/1 | 0/1 | 0/1 | 0/1 | 0/1 | 0/1 | tm/nm |

FIG. 19

EXTENDED REALITY MEDICAL REPORT GENERATING SYSTEM

CROSS-REFERENCE TO RELATED APPLICATION(S)

This application is a U.S. National Stage filed under 35 U.S.C. § 111(a), which is a continuation of and claims priority to International Application No.: PCT/US2019/019598, filed Feb. 26, 2019, designating the United States and published in English, which claims the benefit of and priority to U.S. Provisional Application No. 62/635,355, filed Feb. 26, 2018, the entire contents of each of which are incorporated herein by reference.

FIELD OF THE INVENTION

The present invention relates to systems and methods suitable for medical report generation. In particular, the present invention relates to systems and methods for generating representative medical reports for viewing in augmented reality environments.

BACKGROUND

Medical technology has improved dramatically in recent years, with many diagnostic tools incorporating cameras and other imaging systems to peer inside the human body. These tools are used by doctors to diagnose, treat, and track patient progress. As the tools have become more complex, the views of systems and organs within the body have become clearer, giving healthcare providers a view of structural abnormalities, tumors, lesions, and other clinical findings. In some cases, diagnostic cameras move through the body to record video of the organ function and display tissue health. One example of this technology focus is endoscopic procedures that pass a scope through the gastrointestinal tract, pinpointing abnormalities and disease. Another technology seeing increasing use is three-dimensional ultrasound.

While the technology has improved, medical reports have increased in complexity. Healthcare professionals may readily understand the clinical findings presented in a report and will immediately relate the abnormalities seen on the video with the location on the body. The patient however, may have less understanding of where the disease or condition occurs and may not be able to visualize how their particular condition affects normal functioning.

At the same time as medical imaging technology improved, so have computer rendering and three-dimensional video techniques. Virtual reality systems have been used to provide immersive experiences that allow users to move through a multi-projection environment and view realistic images. A viewer may "look around" the virtual world and interact with it, typically while wearing a head-mounted display unit with a small screen in front of their eyes. Such virtual worlds may use the same video or photo inputs for each user, with customization occurring as a user moves through the virtual world.

Patients often receive only a two-dimensional, jargon-filled report from their healthcare provider, leaving them with many questions and concerns. Current medical materials are intended to document conditions and diseases, not facilitate patient understanding. The treating physician may display the endoscopic video or the scan output while discussing the test results, however, users are not typically able to access the test results once they leave the medical office or facility. Privacy concerns may hinder the sharing of the data, as medical record theft has become a significant concern, with a number of highly publicized medical data cyber-attacks reported.

There is a need in the art for systems and methods that can present each patient's test results in a clear and educational manner, while ensuring medical record privacy and security.

SUMMARY

Embodiments described herein provide a method for creating a representative tour medical report. The method comprises the steps of: receiving medical findings for a specific patient from a medical records server; entering the medical findings into a virtual reality visualization screen for a segment of a patient's gastrointestinal (GI) tract; repeating entering the medical findings into a virtual reality visualization screen for the segment of the patient's GI tract until all conditions have been entered; and generating an access code for the representative tour medical report.

A further embodiment provides an apparatus for creating a representative tour medical report. The apparatus includes a user terminal in communication with a healthcare provider web application; a secure medical data storage facility in communication with the healthcare provider web application and the user terminal; an anonymizing server in communication with the user terminal, web application and secure medical data storage facility; and a quick response code generator in communication with the user terminal.

A still further embodiment provides a non-transitory computer-readable medium containing instructions, which when executed, cause a processor to perform the following steps: receiving medical findings for a specific patient from a medical records server; entering the medical findings into a virtual reality visualization screen for a segment of a patient's gastrointestinal (GI) tract; repeating entering the medical findings into a virtual reality visualization screen for the segment of the patient's GI tract until all conditions have been entered; and generating an access code for the representative tour medical report.

In accordance with example embodiments of the present invention, a method for creating a representative tour medical report is provided. The method includes, receiving medical findings for a specific patient from a medical records server, entering the medical findings into a virtual reality visualization screen for a body part or tract, repeating the entering the medical findings into a virtual reality visualization screen for the body part or tract until all conditions have been entered, and generating an access code for the representative tour medical report.

In accordance with aspects of the present invention, the entering the medical findings into a virtual reality visualization screen for the body part or tract comprises pinning localized medical findings to a designated pin in the virtual reality visualization screen. The localized medical findings can be locations on a specific patient and relate to at least one of: gastrointestinal tract, cardiac system, vascular system, oral, and esophageal systems. Entering the medical findings into a virtual reality visualization screen for the body part or tract can include painting diffuse medical findings to the body part or tract.

In accordance with aspects of the present invention, the entering medical findings into a virtual reality visualization screen for a sub-segment of the patient's body tract can include entering findings for at least one of the following segments: esophagus, stomach, duodenum, upper GI, lower GI, transverse colon, ascending colon, cecum, terminal ileum, descending colon, sigmoid, and rectum. Both the upper GI and lower GI tract can be composed of multiple segments. Each of the multiple segments form a representation of the patient's GI tract has localized conditions and diffuse conditions. The method of creating the representative tour can be repeated for multiple segments of the patient's GI tract, forming an end-to-end tract of the patient's GI tract.

In accordance with aspects of the present invention, the method can further include sending the access code for the representative medical report to the specific patient. The method can further include providing the specific patient with a choice to view a generic virtual medical tour related to the specific patient's medical condition or to view the representative tour customized for the specific patient.

In accordance with example embodiments of the present invention, an apparatus for creating a representative medical report. The apparatus can include a user terminal in communication with a healthcare provider web application, a secure medical data storage facility in communication with the healthcare provider web application and the user terminal, an anonymizing server in communication with the user terminal, web application, and secure medical data storage facility, and a quick response code generator in communication with the user terminal.

In accordance with aspects of the present invention, the healthcare provider web application can incorporate pinning and painting tools to allow the user to create a customized representative medical report. The healthcare provider web application can incorporate tools for joining multiple affected segments from a specific patient's body tract together. The healthcare provider web application tools for joining multiple affected segments of the specific patient's body tract together can use fades to affect a teleporting experience.

In accordance with example embodiments of the present invention, a non-transitory computer-readable medium containing instructions can be provided. The instructions, when executed, cause a processor to perform the steps of receiving medical findings for a specific patient from a medical records server, entering the medical findings into a virtual reality visualization screen for a body part or tract, repeating the entering the medical findings into a virtual reality visualization screen for the segment of the body part or tract until all conditions have been entered, and generating an access code for the representative tour medical report.

In accordance with aspects of the present invention, the non-transitory computer-readable medium can further include instructions for entering the medical findings into a virtual reality visualization screen for the body part or tract and pinning localized medical findings to a designated pin in the virtual reality visualization screen, wherein the body part or tract is a gastrointestinal (GI) tract.

The non-transitory computer-readable medium can further include instructions for entering the medical findings into a virtual reality visualization screen for the body part or tract comprises painting diffuse medical findings to the selected segment of the patient's GI tract. The non-transitory computer-readable medium can further include instructions for entering findings for at least one of the following sub-segments of the tract: esophagus, stomach, duodenum, upper GI, lower GI, transverse colon, ascending colon, cecum, terminal ileum, descending colon, sigmoid, and rectum.

BRIEF DESCRIPTION OF THE DRAWINGS

Other systems, methods, features, and advantages of the presently disclosed embodiments will be or will become apparent to one with skill in the art upon examination of the following figures and detailed description. It is intended that all such additional systems, methods, features, and advantages be included within this description, be within the scope of the presently disclosed embodiments, and be protected by the accompanying claims. Component parts shown in the drawings are not necessarily to scale and may be exaggerated to better illustrate the important features of the presently disclosed embodiments. In the drawings, like reference numerals designate like parts throughout the different views, wherein:

FIG. 19 is a table of selection variables for use by a healthcare professional in preparing a medical report for a patient, in accordance with an embodiment of the application.

DETAILED DESCRIPTION

Figure 1:
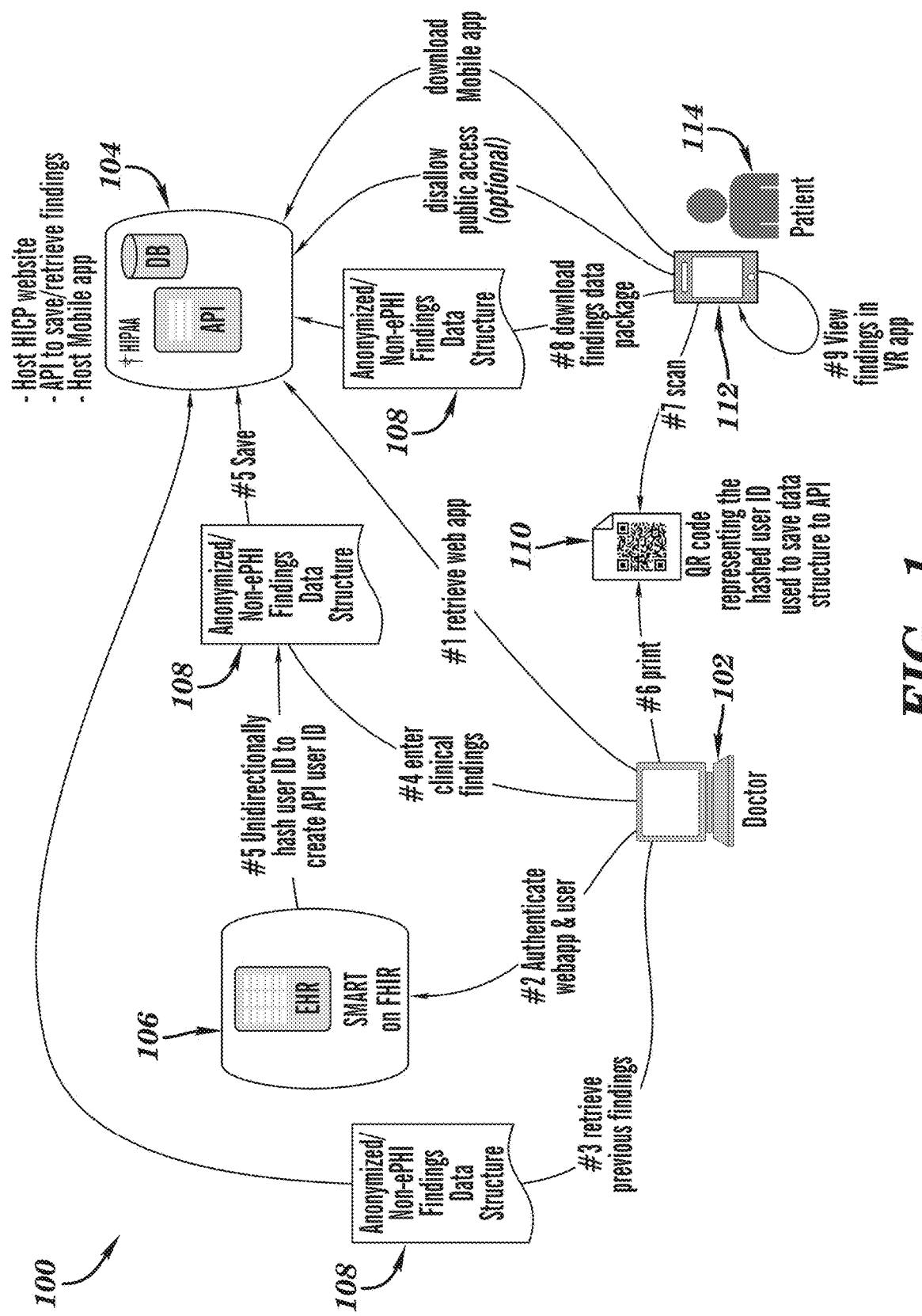
FIG. 1 shows a system architecture of a medical report generator, in accordance with an embodiment of the application.

The detailed description of exemplary embodiments herein makes reference to the accompanying drawings and pictures, which show the exemplary embodiments by way of illustration and its best mode. While these exemplary embodiments are described in sufficient detail to enable those skilled in the art to practice the presently disclosed embodiments, it should be understood that other embodiments may be realized, and that logical and mechanical changes may be made without departing from the spirit and scope of the presently disclosed embodiments. Thus, the detailed description herein is presented for purposes of illustration only and not of limitation. For example, the steps recited in any of the method or process descriptions may be executed in any order and are not limited to the order presented. Moreover, any of the functions or steps may be outsourced to or performed by one or more third parties. Furthermore, any reference to singular includes plural embodiments, and any reference to more than one component may include a singular embodiment.

The present invention implements a unique combination of steps to solve a technical problem in the medical field. It has been a long-standing problem for medical professionals to properly explain medical issues with patients. Advances in technology has creates more technical tests and technical test results, adding to the difficulty for explaining results in a manner that is easily understood and visualized by patients. The present invention utilizes a combination of technological advances, not previously available, and a unique combination of steps to yield a novel approach for guiding a patient through test results and explaining findings within a medical procedure. The combination of steps provided by the present invention are tied to a computer architecture such that they could not be performed by a human alone unassisted. The computer implemented steps also enable a practitioner to efficiently and easily review test, imaging, and procedure results to create a virtual medial tour for review by a patient. Such advantages allow a practitioner to treat and effectively explain issues to patients in a timely manner, not previously achievable. Therefore, the present invention improves patient understanding of medical processes and enables a practitioner to more effectively use their time and allow more time to effectively treat more patients while leaving patients more satisfied with the medical explanations.

Embodiments disclosed herein describe a method and system architecture of a medical report generating system. The medical report generating system can be configured to provide both conventional medical reporting's as well as a computer generated medical tour for a particular procedure(s) performed on the patient. In some embodiments, the computer generated medical tour can be an extended reality format, for example mixed, augmented, or virtual reality, tour of a bodily system or organ that a procedure was performed upon with embedded annotations provided by a healthcare professional performing and/or reviewing results of said procedure. The architecture can incorporate three components: a healthcare provider front end application, a patient mobile device application, and an intermediary web service tying the healthcare provider front end application and the patient mobile device application together.

In some embodiments, the healthcare provider application can enable a medical provider to find a patient within a patient database and construct a computer-generated representation of the findings of a procedure for viewing by that patient. While the figures illustrate an endoscopic procedure performed with a video camera, it is contemplated that other procedures and scan tools may be used and that other parts of systems of the human body may be the subject of a computer generated medical tour. As an example, any combination of two-dimensional and three-dimensional ultrasound images, magnetic resonance imaging (MRI) scan images, X-ray images, videos, etc. may also be used to create the computer generated medical tour. Similarly, any combination of systems, organs, or parts of the human body can be represented utilizing the present invention and is not limited to the examples provided herein. For example, virtual tours of the circulatory, respiratory, digestive, excretory, nervous, endocrine, immune, integumentary, skeletal, muscle, and reproductive systems, or any subsets thereof, can be conveyed to a user. In some embodiments, the computer generated medical tour can be an augmented reality, for example virtual reality, tour through the systems, organs, or parts of the human body that the two-dimensional and three-dimensional images or videos were captured during a procedure(s).

In some embodiments, the computer-generated representation of a procedure(s) constructed by the healthcare provider can be based on the clinical findings of a procedure or scan performed on a patient and can be unique to a particular patient at a particular point in time. The virtual tours may be constructed for successive procedures of the same type, giving a patient a view of ongoing changes in their condition.

In accordance with embodiments of the present invention, Fast Healthcare Interoperability Resources (FHIR) can be utilized as part of a standard that describes data formats and elements (known as "resources") and an application programming interface (API) for exchanging electronic health records. FHIR utilized by the present invention can be built on a web-based suite of API technology and can use hypertext transfer protocols (http), representational state transfer (REST) for interoperability between computer systems on the Internet, hypertext markup language (HTML), and Java Scrip Object Notation (JSON) or extensible markup language (XML), and cascading style sheets. As would be appreciated by one skilled in the art, similar programs offering similar functionality may be incorporated without departing from the spirit and scope of the application.

In some embodiments, the web service component of the present invention can be configured to utilize and store the same data packet that was sent to the FHIR patient database and can provide endpoints for the patient mobile application to fetch or destroy the data. The patient mobile application can fetch the patient data from the web site to render the augmented reality experience of the computer generated medical tour.

For the computer generated medical tour, the present invention can utilize augmented reality, including virtual reality environments, to provide a computer-generated scenario that simulates a realistic experience that can be an immersive experience for the user. This immersive environment may be similar to the real world to create a lifelike experience that is grounded in reality, in the present invention, the reality of the patient's own body. Typically, users experience virtual reality using virtual reality headsets, but the present invention contemplates providing a two-dimensional or three-dimensional virtual rending on a desktop, laptop or mobile device screen, in addition to a virtual reality headset. Augmented reality systems layer virtual information over a live camera feed into a headset, or through a computer, smartphone or tablet device. Different embodiments of the application may use either virtual reality or augmented reality features and devices, based on the medical imaging tools used in the screenings used to generate the representative medical report.

FIG. 1 illustrates an exemplary embodiment for an architecture for a representative medical reporting system in accordance with embodiments described herein. System architecture (100) can provide interfaces between a doctor or healthcare provider's computer or input device (102) and a Fast Healthcare Interoperability Resources (FHIR) website (104) using a self-monitoring analysis and reporting (SMART) protocol. In some embodiments, the FHIR website (104) can be a healthcare provider website that includes access to an application programming interface (API) and a database. The API within host healthcare provider website (104) can enable a user to securely save and retrieve reported findings for specified patients.

The system architecture (100) can also provide a self-monitoring analysis and reporting (SMART) FHIR application (106) that can be accessed by doctor's computer (102). As would be appreciated by one skilled in the art, the patient data findings or test results may be stored in an anonymizing non-electronic permanent health insurance (non-ePHI) data structure (108) that stores this data in accordance with accepted medical data storage policies and procedures. In some embodiments, a hashed patient identification (ID) code (110), or other machine-readable objects, can be used for creating and accessing the representative medical report over multiple devices in the architecture (100). For example, the hashed patient identification (ID) code (110) can be a Quick response (QR) code used by devices to retrieve a medical record or medical tour. Similar to the computer (102), a computing device (112), such as a desktop, laptop or mobile device, may be used by patient (114) to access the representative medical reports and/or computer generated medical tours.

In operation, the doctor's computer (102) can be communicatively attached to the architecture (100) (e.g., over a network or the Internet) and access the website (104), the FHIR application (106), and the other data structures (108). For example, a user can use the computer (102) to access a Uniform Resource Locator (URL) address associated with the present invention to access and/or retrieve the web application from the host health care provider website (104). The web application can include access to the API and a database including the electronic heath records within the architecture (100). Once the web application is retrieved, the computer (102) can request access to the SMART or FHIR (106), and the SMART or FHIR (106) can authorize the computer (102) web application and the user, for example, the doctor. The authorization can be based on any combination of systems and methods known in the art. For example, the authorization can be based on user credentials (e.g., user name and password), a Media Access Control address (MAC address), an exchange of public and/or private keys, etc. or any combination of methods or systems known in the art. Once authorized, a user can stay logged into the system and authorized throughout the session.

Once the computer (102) has accessed the web application, the user can perform various read and write transactions within the architecture (100), based on authorization levels. For example, the user can retrieve previous procedural findings from an anonymizing data structure (108) within the architecture (100) for comparison, or to create a more comprehensive medical report. The anonymizing data structure (108) may interface with healthcare provider website (104) in a secure manner throughout this process. The doctor may also enter clinical findings and submit them to the anonymizing data structure (108) through the web application of the website (104) for others to use their findings/test results.

In some embodiments, the anonymizing data structure (108) anonymizes the data by unidirectionally hashing a user identification (ID) to create an API user identification. The hashing can be performed using any combination of systems and methods known in the art. The hashed user ID (110) can be transformed into a format to be shared with another user. For example, the hashed patient ID (110) can be transformed into an encoded human and/or machine-readable format, such as a Quick Reference code (QR code), a barcode, an encrypted string, etc. and shared with another user (e.g., a patient) by printing, texting, emailing, etc. the patient (110). The patient (114) can enter or scan the patient ID (110), using another computing device (112), to receive access to a representative medical report associated with said patient ID (110). For example, using an application associated with the website (104) or using the web application from the website (104), the computing device (112) can be used to scan a QR code to transmit the hashed ID to the website (104) and receive the representative medical report associated with the patient ID (110) from the anonymizing data structure (108). The representative medical report can be provided to the user on the computing device (112) through the application or the web application. The computer generated medical tour can include any combination of two-dimensional or three-dimensional images, videos, and augmented reality environments that the user can view in the patient application on device (112) to further understand the procedure performed and/or results of said procedure.

The healthcare provider website application (104) can provide an interface for a healthcare provider to find a specific patient within the database and construct a representation of that patient's body system at issue, for example, the gastrointestinal system for visualization by the patient. As would be appreciated by one skilled in the art, any combination of systems within the human body may be used, and veterinary use may also be possible. The representation created by the healthcare provider may be sent to both the patient database for future use and also to the web service for later retrieval by the patient application. The web service stores the same data packet that was sent to SMART FHIR database (106) and provides endpoints for the patient mobile application to either fetch or destroy the data. In some embodiments, the packet can include a JSON string that contains de-identified list of findings and associated positional data. In particular, a hash can be sent to each endpoint to either fetch or destroy the data.

The patient mobile application can be configured to fetch the patient data from the web service to populate the representative medical report or computer generated medical tour. The representative medical report or computer generated medical tour can be provided to help the patient understand the issues identified during a test or procedure using an augmented reality experience on patient computing device (112). The website application (104) may also allow a patient or user to download an application compatible with the operating system of their mobile device and may also disallow public access to the application, if desired. As would be appreciated by one skilled in the art, all data stored within the architecture (100) and accessed by devices (102), (112) can include data that has been anonymized with all protected health information (PHI) and/or personally identifiable information (PII) removed.

Figure 2:
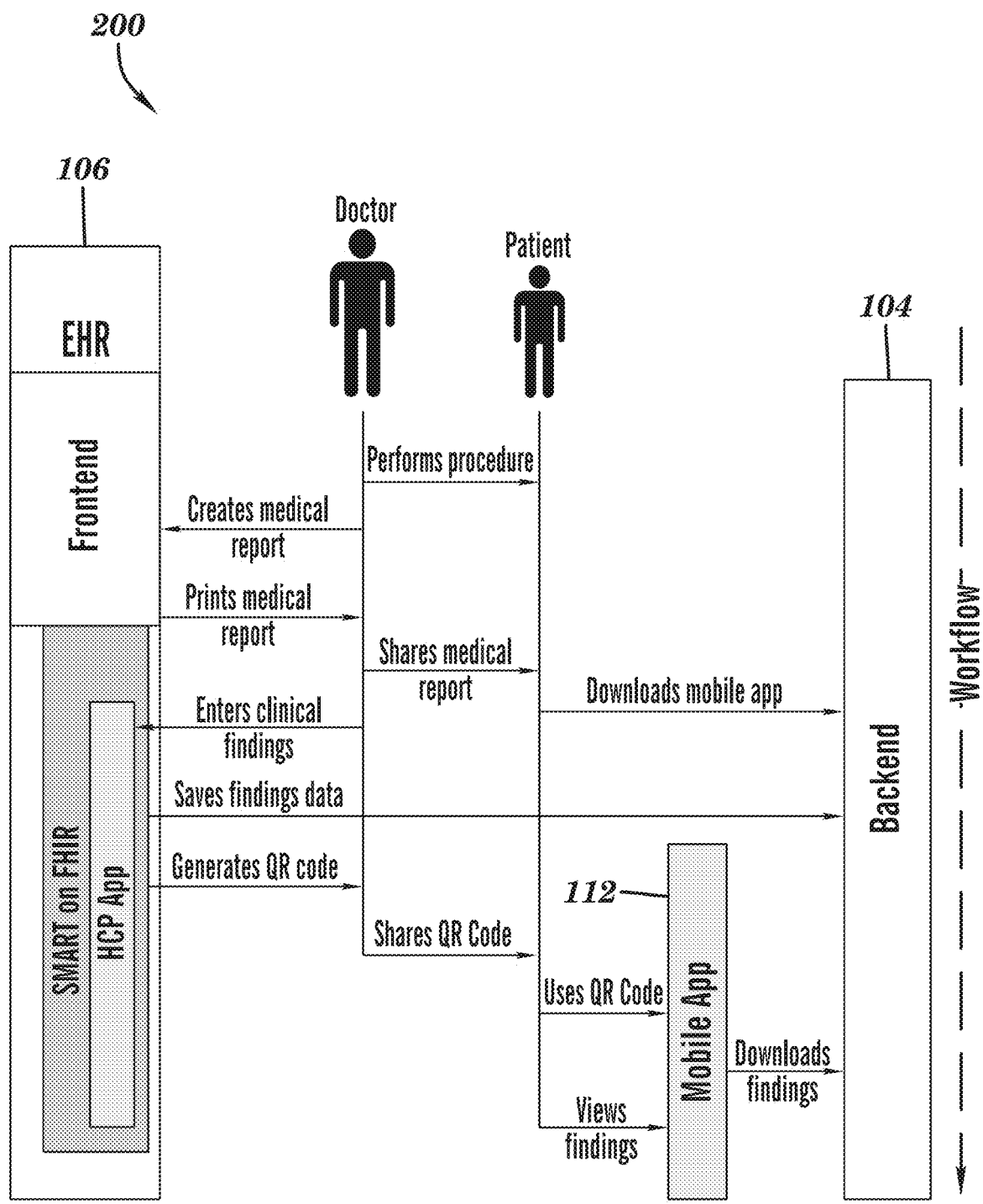
FIG. 2 shows a workflow for a medical imaging report system, in accordance with an embodiment of the application.

FIG. 2 depicts an exemplary workflow that can be used to create a representative medical report. Initially, the doctor or other health professional can perform a scan or comparable procedure on a patient in a normal course of business. After the conclusion of the procedure, the doctor can create a medical report, and print the medical report. The medical report can be an electronic health record (EHR) that is accessible on the SMART FHIR, that in turn supports the healthcare provider (HCP) application. The doctor can share the printed medical report with the patient during a follow-up consultation to discuss the procedure results. The doctor can also enter the clinical findings into the HCP application. The clinical findings can be provided to a backend application that provides the patient access to the generated representative backend application.

In some embodiments, the representative medical report can include some combination of a traditional medical record and a computer generated medical tour of a portion of the patient's body. For example, the representative medical report can include an augmented reality tour of the patient's body with annotations made by the doctor located at various locations throughout the tour. The annotations can be used by the doctor to note areas of interest/concern that were identified as part of the medical procedure (e.g., endoscope, imaging, exploratory surgery, etc.). The tour is intended to provide a patient unique insight into what is happening with their body outside of traditional verbal and written explanations.

The HCP application can generate the patient ID (110) and provide it to the doctor, who can provide the patient ID (110) to the patient or the patient ID (110) can be directly provided to the patient. In some embodiments, upon receipt of the patient ID (110), the mobile application on the patient's computing device (112) can download the clinical findings form the backend portion of the system architecture (100). The patient can then use the patient ID (110) in the mobile application to view the clinical findings. As would be appreciated by one skilled in the art, the backend portion of the system architecture (100) can be configured to be compliant with the requirements of the Health Insurance Portability and Accountability Act (HIPAA) and other medical record standards that specify detailed privacy requirements for medical data storage and access.

The embodiments described below provide dynamically created two-dimensional and three-dimensional renderings and sequencing to create the representative medical report. In some embodiments, computer generated virtual reality visualizations are created and a user can enter any findings through a user interface, as described in greater detail herein. For example, the system 100 can generates a virtual reality version of the selected anatomy via a JSON file. As would be appreciated by one skilled in the art, the video from procedures and/or images from medical imaging technology can be used to create the immersive three-dimensional view of the medical representation that the patient accesses via a mobile or virtual reality device. For example, in augmented reality visualization, the video can be a 360 degree video labeled for anatomical location by the user (e.g., a healthcare practitioner). Using the medical representation, the user can tour their own body and see the specific conditions and areas of concern or treatment annotated by the treating physician. Any type of two-dimensional and/or three-dimensional augmented reality or virtual reality system may be incorporated into the embodiments described herein.

In some embodiments, the healthcare provider front end interface can be compatible with major internet and browser applications and can be accessed via a desktop, laptop computer, or mobile device. Similarly, the patient-facing web service application can operate on most virtual reality platforms and can be compatible with mobile devices such as smart phones and tablets.

The healthcare provider front end can be used by healthcare professionals during or after a medical procedure to document the location of issues found. In some embodiments, the locations can be entered via drag and drop for each anatomy, system, organ, region, etc., thereafter, the locations can be visible overtop the anatomy diagram as icons. After the procedure, and optionally after documentation, the front end can be used to produces a portable document format (PDF) of the findings to share with the patient. In some embodiments, the healthcare provider front end runs in an environment that does not require a login functionality and also assists in selecting the patient. In one example, the environment of the healthcare provider application may start with the patient already in the scope (e.g., an endoscope, colonoscope, etc.). Once a user, such as a doctor, launches the scope, they are presented with a landing page. The landing page presents a short description with a short description of what the program does, as well as a list of steps needed to create a patient representative medical record or computer generated medical tour to be shared with a patient over a patient-facing application.

In some embodiments, the patient-facing application may be used with patients with a variety of medical conditions over any combination of body systems, organs, or body parts. For example, the present invention can be utilized for gastrointestinal (GI) diseases such as Crohn's disease or colitis is used. As would be appreciated by one skilled in the art, the GI examples are for demonstration purposes in this application, and the application is not limited to use solely with one condition. Any medical imaging procedure may be used to produce a representative medical report. The representative medical report or computer generated medical tour, provided in the platform, may be designed assist patients to understand their conditions and track progress, particularly when successive reports illustrate changes in the test results.

Figure 3:
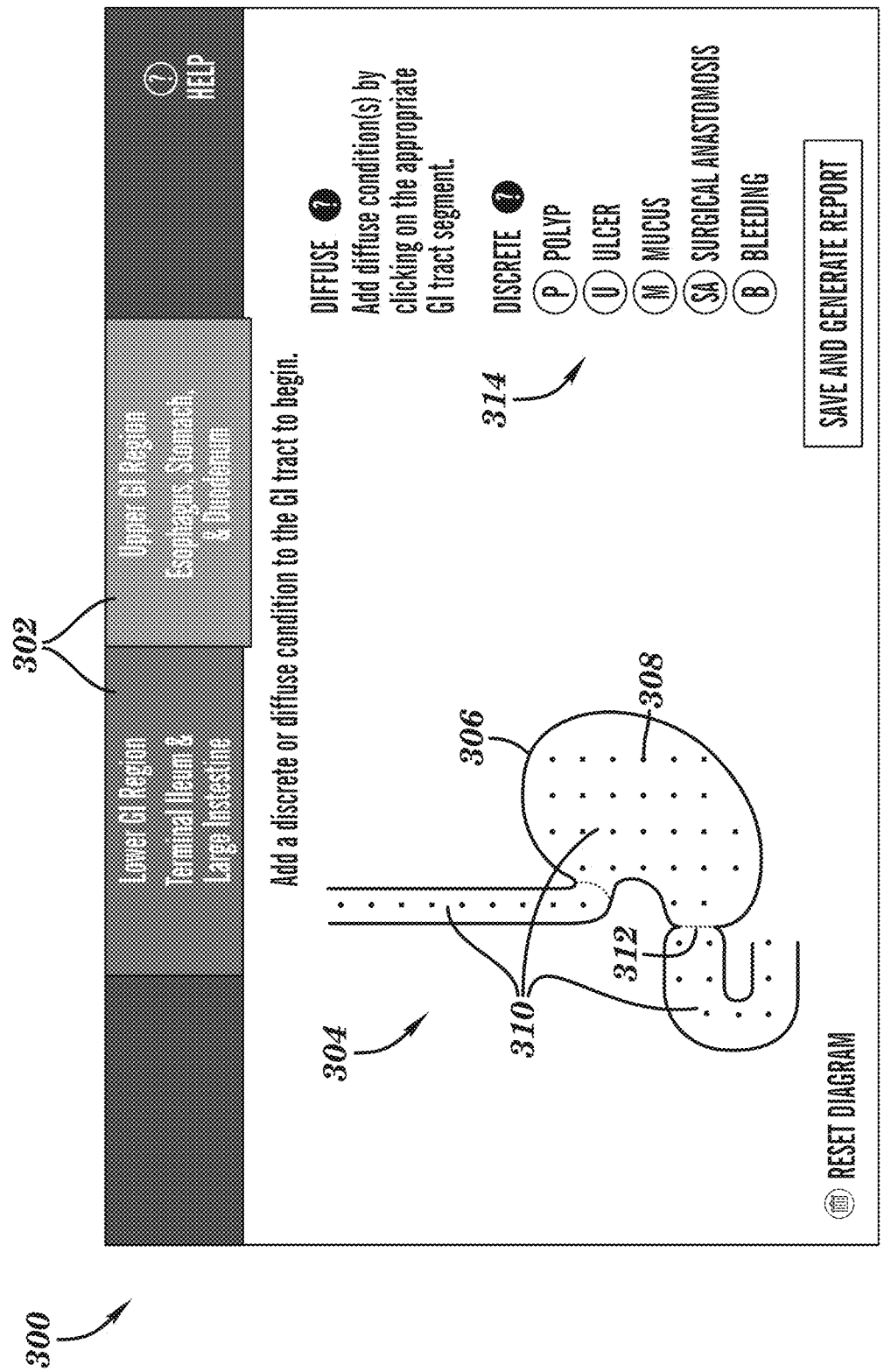
FIG. 3 is a graphical user interface of a healthcare provider screen for a medical imaging report system, in accordance with an embodiment of the application.

FIG. 3. is an exemplary view of a healthcare provider graphical user interface (GUI) (300) for a representative medical report, in accordance with an embodiment of the present invention. In some embodiments, the healthcare provider front end can allow the doctor or healthcare provider to configure a custom medical report for a specific part of the body or body system using the GUI (300). The representative medical report or computer generated medical tour can be an augmented or virtual reality experience based on the procedures and medical imaging performed on the patient and later annotated by the healthcare provider. To configure a custom report, the GUI (300) can present the doctor with options to select a particular body system or body part to be rendered within the GUI (300) for configuration and denotation. The doctor can also be presented with a list of search results in a table, allowing the doctor to choose the desired patient. As would be appreciated by one skilled in the art, the selections can be made using any combination of methods known in the art. For example, the selection can be made from a drop-down menu or list.

In the example provided in FIG. 3, the gastrointestinal region has been selected for configuring a custom gastrointestinal medical report. In some embodiments, the GUI (300) can include tabs 302 for different subsets of the selected region and doctors can select particular subsets of a system or body part. For example, as depicted in FIG. 3, the tabs 302 can include a first tab for the upper gastrointestinal tract including the terminal ileum and large intestine and a second tab for the lower gastrointestinal including the esophagus, stomach and duodenum. FIG. 3 displays an exemplary rendering with the second tab selected and FIG. 4 displays an exemplary rendering with the first tab of the GUI (300) selected. As would be appreciated by one skilled in the art, the present invention can include any combination of bodily regions, body parts, segments, etc. with different tabs 302 for each and is not intended to be limited to the examples provided herein.

In some embodiments, the GUI (300) can present the doctor with a generic diagram 304 or stylized map of a selected body system or region, reflected in the tab selection. For example, as shown in FIG. 3, a generic diagram 304 of the lower gastrointestinal system including esophagus, stomach and duodenum is provided. The generic diagram 304 can include an outline 306 of the selected region reflecting a shape of the selected system, organ, or body part. In some embodiments, a plurality of pegs 308 can be distributed throughout the outline 306 to provide attachment points for annotations of conditions or other notes. The pegs 308 can be utilized to mark specific areas of note within the selected region, as discussed in greater detail herein. In alternative embodiments, the generic diagram 304 can be empty and allow the placement of annotations anywhere within the outline 306. Additionally, each of the gastrointestinal tract segments can be further divided into various predefined anatomical segments 310, denoted by segment lines 312, that can be selected and rendered as generic diagrams 304 for those selected segments 310.

Figure 4:
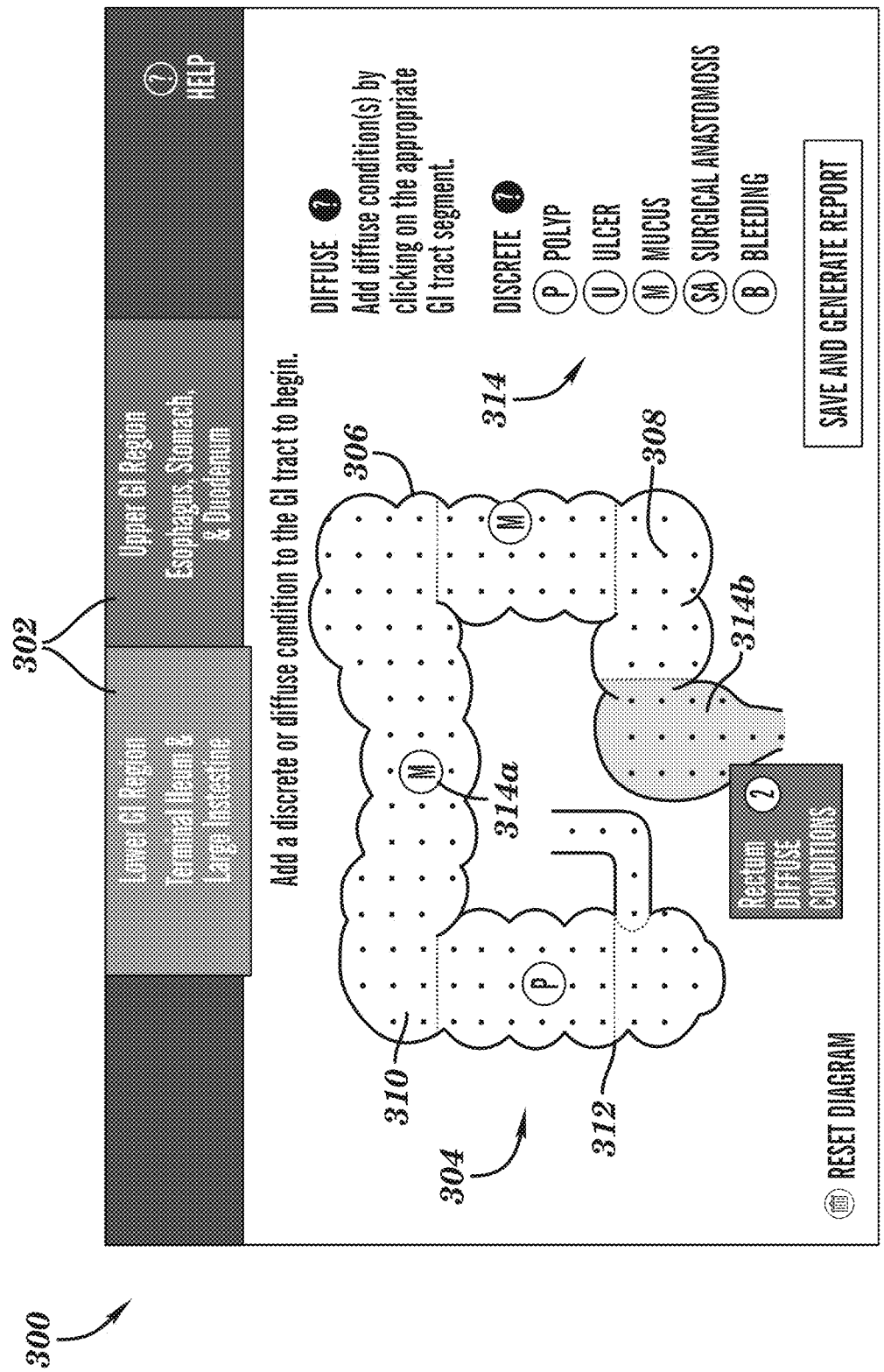
FIG. 4 is a graphical user interface of a healthcare provider screen for healthcare provider input to a medical imaging report system, in accordance with an embodiment of the application.

In some embodiments, condition makers 314 can be applied to locations within the generic diagram 304. The condition markers 314 can correspond to discrete conditions 314a and diffuse conditions 314b can be presented to the doctor in the GUI 300. The discrete conditions 314a can differ from diffuse conditions 314b in that discrete conditions 314a may be applied to an individual peg 308 within the selected segment 310, for example, by dragging a discrete condition symbol to a peg 308. In contrast, the diffuse conditions 314b can be applied to entire regions within the generic diagram 304. In some embodiments, the GUI 300 can present the doctor with a predetermined list of discrete conditions 314a that can be applied to the pegs 308 within the generic rendering. For example, as depicted in FIGS. 3 and 4, the discrete conditions 314a can be polyp, ulcer, mucus, surgical anastomose, and bleeding. As would be appreciated, the predetermined conditions can vary based on the selected region, segment 310, body part, etc. as defined by associations stored in the database.

In some embodiments, each peg 308 may only contain one condition and discrete conditions 314a may not be applied to a segment 310 as a whole. For example, should a user attempt to drag a discrete condition onto a peg 308 that is already occupied, the icon being dragged changes to an indicator showing that the condition may not be placed at that location. The doctor may drag the discrete condition to other vacant pegs 308 if needed. To remove a discrete condition, when the doctor begins dragging a previously placed condition icon a box (e.g., trashcan icon) occurs providing the option to delete the condition. In some embodiments, throughout the processes, a hint system can be provided to guide the doctor through the use of the scope tool. Additionally, popup help windows can be implemented to provide ongoing assistance and may be customized to the body part or tract being modeled.

Referring to FIG. 4, an exemplary view of a healthcare provider GUI (300), with the first tab selected is depicted. FIG. 4 displays a generic rendering of the terminal ileum and large intestine with multiple discrete conditions 314a selected and a single diffuse selected. For example, FIG. 4 shows a lower GI with a poly and two mucus discrete conditions 314a placed thereon. In some embodiments, the doctor can be presented with and select specific diffuse conditions 314b to be displayed on the generic rendering of a particular patient. For example, the doctor can select a desired segment 310 within a generic diagram 304 and choose a diffuse condition to apply to that segment 310, as depicted in FIG. 4. Each condition button can act as a toggle with the ability to be turned on or off. The "Apply" button adds the conditions to the selected segment 310 and then presents highlighted view of the affected/selected segment 310 and the name(s) of the diffuse conditions 314b on the in that segment 310 of the generic diagram 304. The doctor may reselect the segment 310 to present the model, populated with the conditions already present in the selected segment 310.

In some embodiments, at any time during the configuration process the doctor may save their progress and upload the current document to both the FHIR patient database and the web service. As would be appreciated by one skilled in that, when editing, creating, and saving medical information, the architecture can encrypt and de-identify any medical data in accordance with known standards. If the user does not save their progress, progress may be lost between sessions. Within the GUI (300), a "last saved" label can be present and shows the doctor when the configuration was last saved. The GUI (300) can also include a "reset diagram" button that can be configured to removes all conditions applied to the currently selected region. In some embodiments, any changes the user makes within the GUI (300) will not effect on the data stored in the server, until the user actively saves the changes.

In some embodiments, once a representative medical report is created and saved, the architecture (100) can transform the medical report into a computer generated medical tour. The computer generated medical tour can be a two-dimensional or three-dimensional tour of a medical procedure and/or a bodily system, segment 310, organ, body part, etc. of a patient in which a procedure and/or imaging was performed. The computer generated medical tour can utilize video and image data obtained during the procedure and imaging and combine the video and images with the annotations provided by the doctor, as discussed in FIGS. 3 and 4. In some embodiments, the front end of the architecture (100) can correlate the denoted condition markers, and the locations thereof, to the same locations within the videos or images obtained during the procedure/imaging. Once the appropriate locations in the images or videos are identified, the front end can overlay computer generated images over the real-world images/videos to create an augmented reality, mixed, reality, or virtual reality display of the procedure within the patient. In some embodiments, a generic modeling for each bodily system has been created and the front end can utilize the conditions added by the user in FIGS. 3 and 4 to customize the generic modeling for viewing by a patient.

Figure 5:
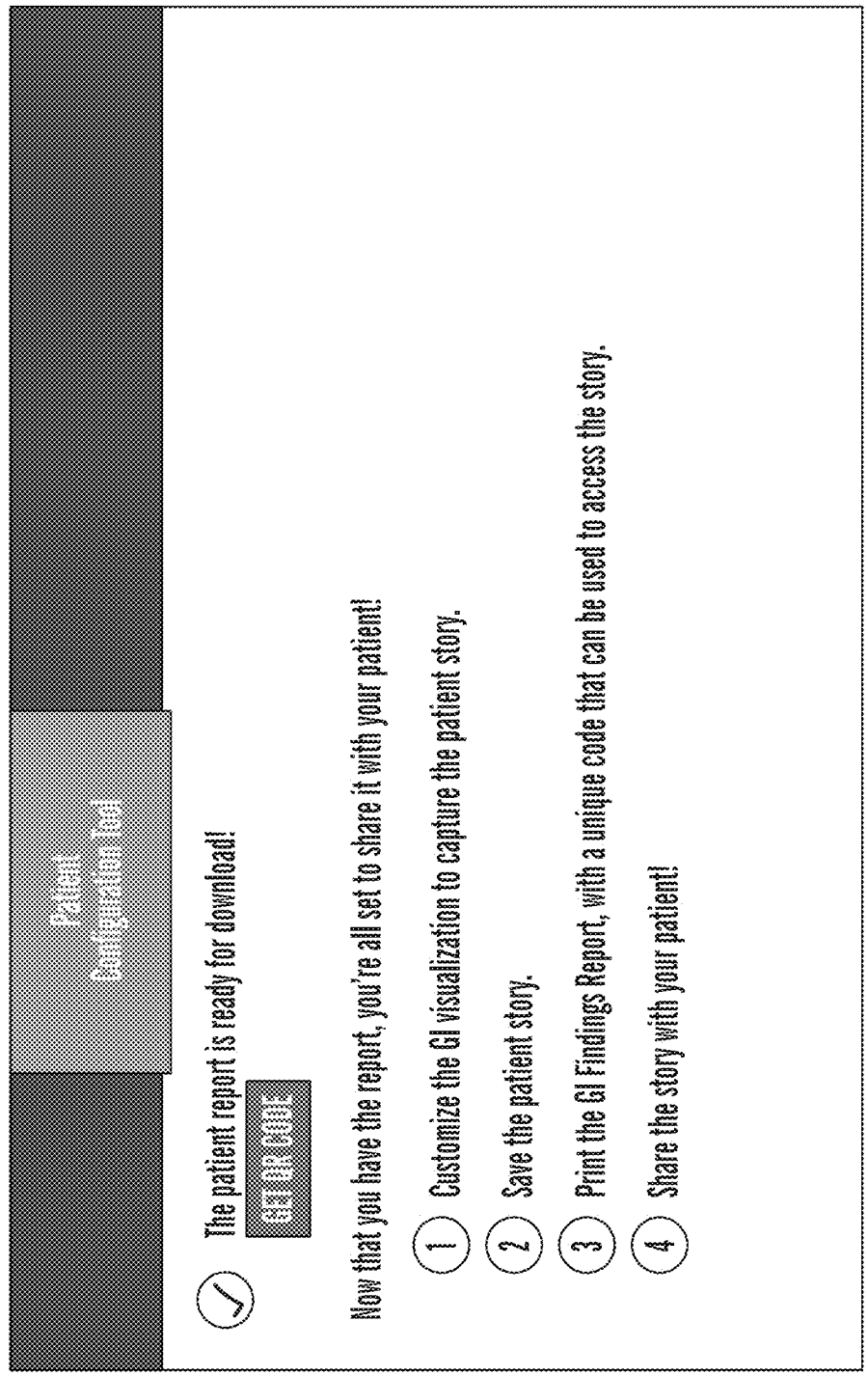
FIG. 5 is a graphical user interface of a download screen for a healthcare provider to use in preparing a medical report, in accordance with an embodiment of the application.

Referring to FIG. 5, an exemplary view of a healthcare provider GUI (300) used to generate a patient ID (110) (e.g., a QR code) for sharing an electronic medical record with a patient. The "generate report" button is active when a medical record has been saved and at least one condition has been applied to a diagram 304. The conditions can be available as a drag and drop icon and can be predetermined conditions stored in the database that are associated with a specific disease and/or procedure. If the doctor presses this button before saving, the scope tool saves automatically. At this point, prior to creating the patient ID (110) for the patient, the doctor has the opportunity to attach notes to the document. The PDF documenting the doctor's findings, along with the patient ID (110) for the patient are then generated and the doctor is brought to the download/print page, shown in FIG. 6. At this point, a doctor may get their report and then return to a search screen to configure the scope tool for a different patient.

Figure 6:
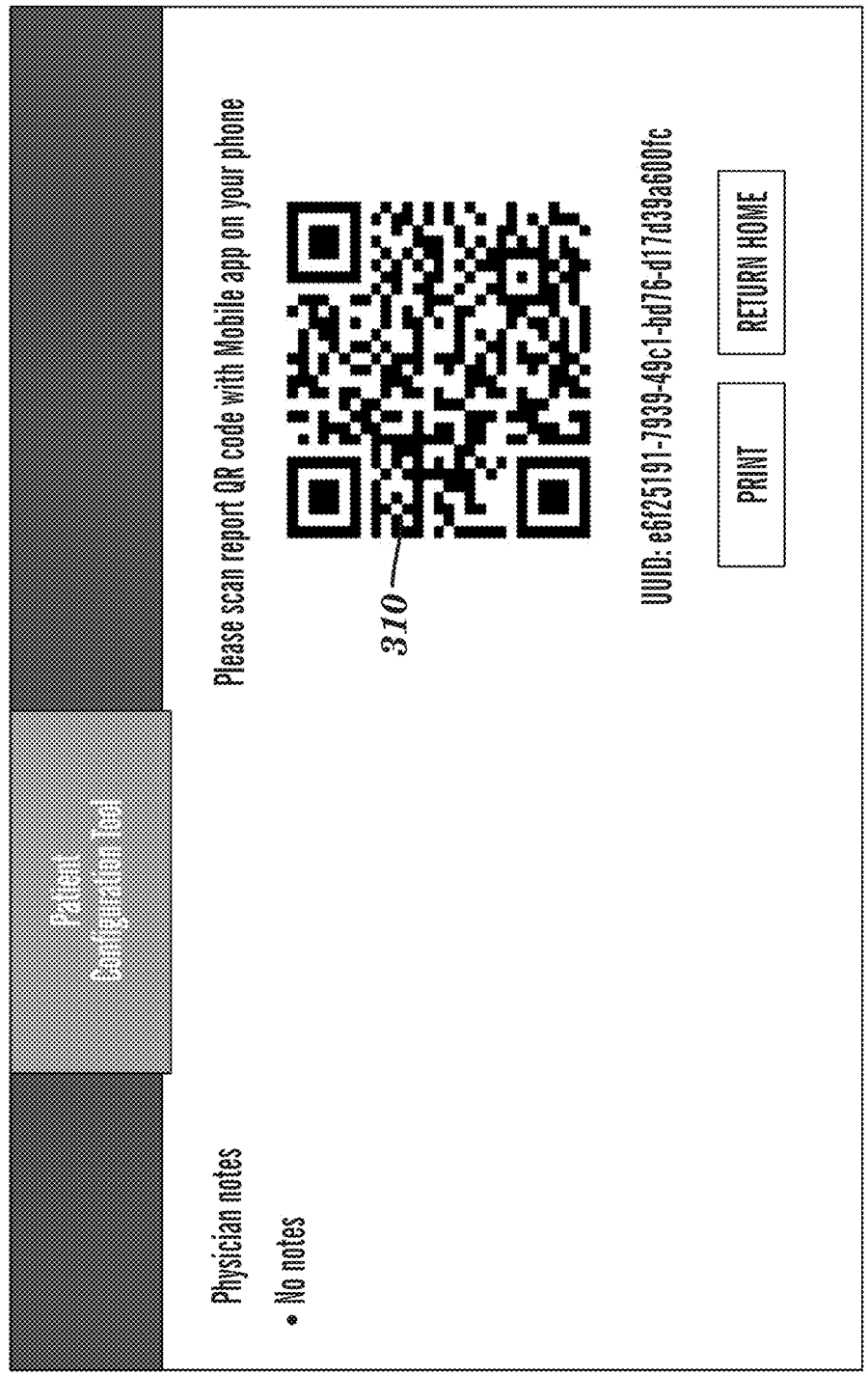
FIG. 6 is a graphical user interface of a code used to access a medical report, in accordance with an embodiment of the application.

Referring to FIG. 6, an exemplary view of a healthcare provider GUI (300) showing the generated the patient ID (110) (e.g., a QR code) to be used by the patient to access the electronic patient record via the patient-facing mobile application or virtual reality device to view their unique representative medical report. After generating the patient ID (110) using the GUI (300) in FIG. 5, the generated patient ID (110) can be transmitted or shared with a patient to enable the patient the ability to retrieve their medical records or medical tours. For example, the doctor can initiate a transmission of the patient ID (110) to the application of the patient, sent via text, email, or it can be printed out to be physically delivered to the patient.

Figure 7:
FIG. 7 is a graphical user interface of a code used to access a medical report, in accordance with an embodiment of the application.

Referring to FIG. 7, an exemplary view of a patient GUI (700) showing the generated the patient ID (110) (e.g., a QR code) to be used by the patient to access the electronic patient record. The patient can take a personalized tour by entering or scanning their personal patient identifier. The personalized tour can be the computer generated medical tour resulting from the representative medical report generated by the doctor, as discussed with respect to FIGS. 3-6. In some embodiments, the GUI (700) can be configured to provide an option to the patient to take a generic tour, perhaps to learn what a normal body system or tract looks like.

Figure 8:
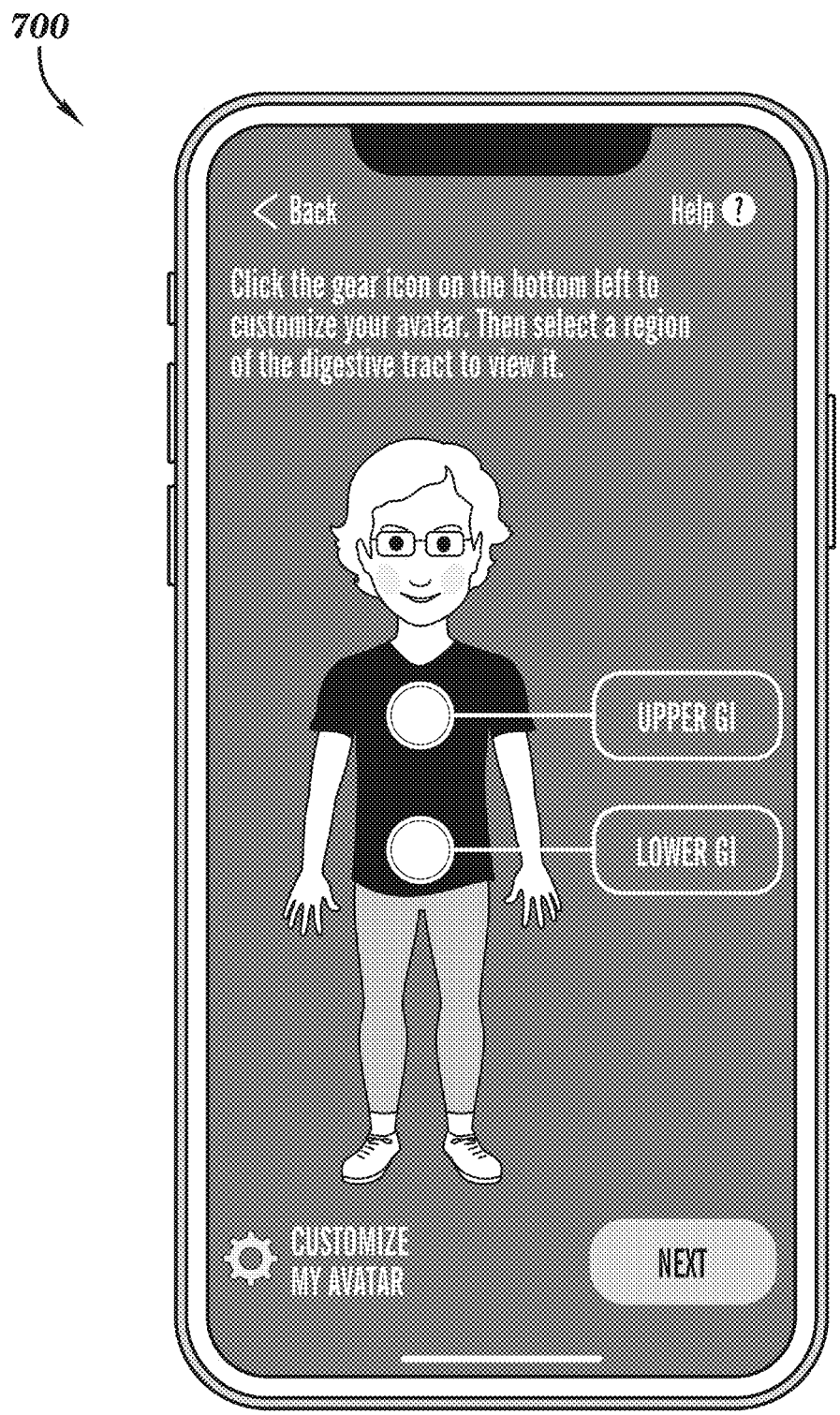
FIG. 8 is a graphical user interface of a user's avatar used in conjunction with a medical report, in accordance with an embodiment of the application.

FIGS. 8-18 provide exemplary graphical user interfaces 700 of a patient facing application used by the patient to access medical information within the architecture (100). Referring to FIG. 8, a graphical user interface of a user's avatar displayed on a patient facing application and used in conjunction with a representative medical report is depicted. The patient-facing application can ask for a name of the user name and prompt whether the user would prefer to view the experience in virtual reality or with swipe navigation. Users may customize their avatar, as shown in FIG. 8 and may change hair, hats, glasses, tops, bottoms, shoes, etc. using methods known in the art. Each of these avatar attributes allows the user to change the color of the item and change the tone of their skin. Once a user has created their character the user then continues to a region selection screen where they can select where they want to go. In FIG. 8, the application provides a user has the option of viewing either an upper gastrointestinal tract (upper GI) or a lower gastrointestinal tract (lower GI). As would be appreciated by one skilled in the art, the application can allow the user to select any combination of bodily systems or body parts to view medical information relevant to those areas, and it not limited to use within the GI example discussed herein. The user makes their selection and the selects the "Next" button to continue on the mobile application. In this example, the use selects the option for upper GI.

Figure 9:
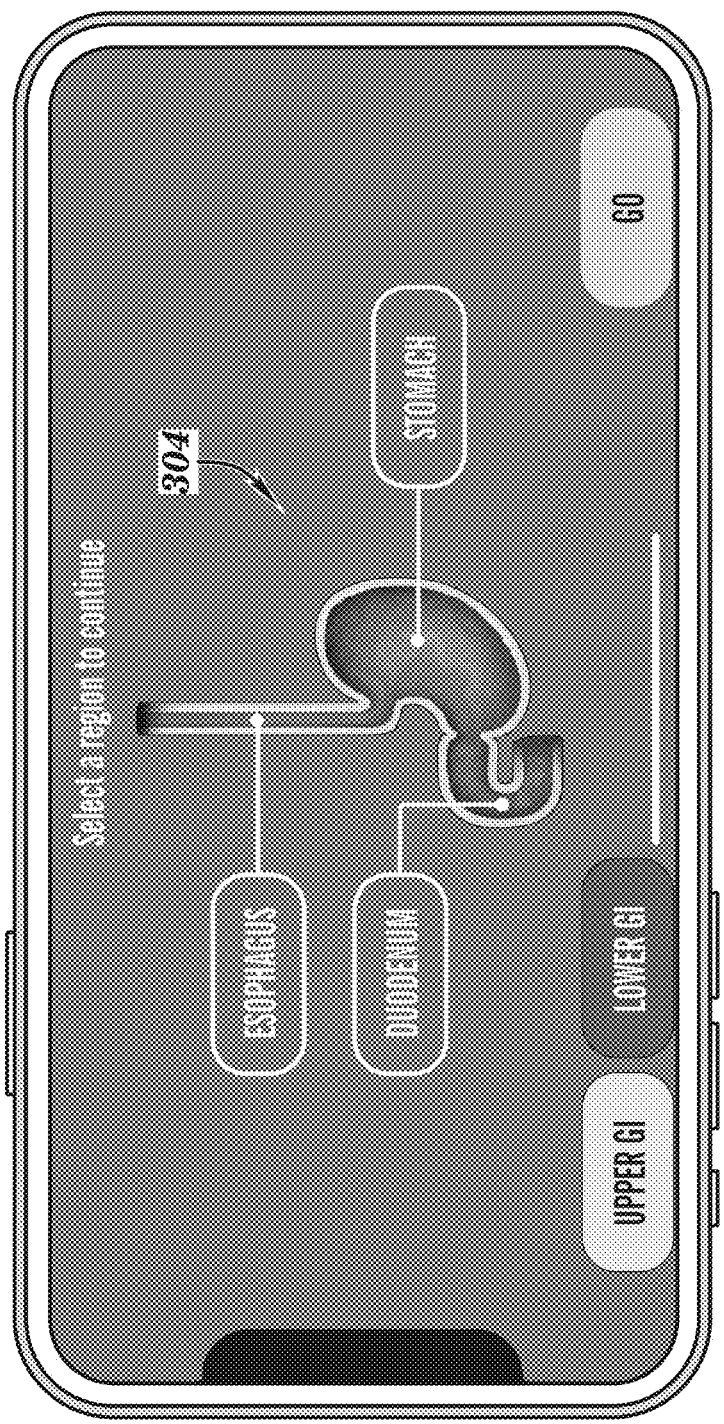
FIG. 9 is a graphical user interface of a user selection screen for selecting a region of anatomy for a virtual medical tour using a medical report, in accordance with an embodiment of the application.

FIG. 9 depicts a graphical user interface 700 of a user selection screen for selecting a region of anatomy for a virtual medical tour using a representative medical report, as discussed with respect to FIGS. 1-6. In some embodiments, this screen can enable a user to select the region to be viewed during the virtual medical tour. As an example, FIG. 9 allows a user to select from three regions: stomach, esophagus, and duodenum, within the upper GI tract previously selected in FIG. 8. In this example, the user initial selects a virtual tour for the duodenum segment of the upper GI.

Figure 10:
FIG. 10 is a graphical user interface of a virtual medical tour selected by a user of a medical report, in accordance with an embodiment of the application.

FIG. 10 depicts a graphical user interface 700 of a computer generated virtual medical tour selected by a user of a representative medical report, in accordance with an embodiment of the application. FIG. 10 shows the view a patient has when viewing the virtual tour. In some embodiments, the tour can include real-world images or videos taken of the user during a procedure with a generic diagram 304 overlay to show the location of the image or video within the selected segment 310. Additionally, computer generated overlays, based on the conditions marked by the healthcare professional, can be rendered within the images or videos to show the user areas of interest or concern.

In some embodiments, while viewing the virtual tour, the user can be teleported from one section to another. During teleporting the screen can fade to a solid color and then fades out, revealing the new section or segment 310 being viewed. As would be appreciated by one skilled in the art, any transitions between sections can be utilized. Initially, the viewer can be positioned in the middle of each section with a clear view of the entire space and any associated conditions located there. In some embodiments, to navigate through the segment 310 or tract, a user can select a "Next" button or a "Previous" button. The use can also navigate and adjust the view utilizing any combination of gestures/motions known in the art, for example, scrolling left or right, pinching inward and outward, etc. At any point, a user may also end the tour and return to the main screen from a menu.

Figure 11:
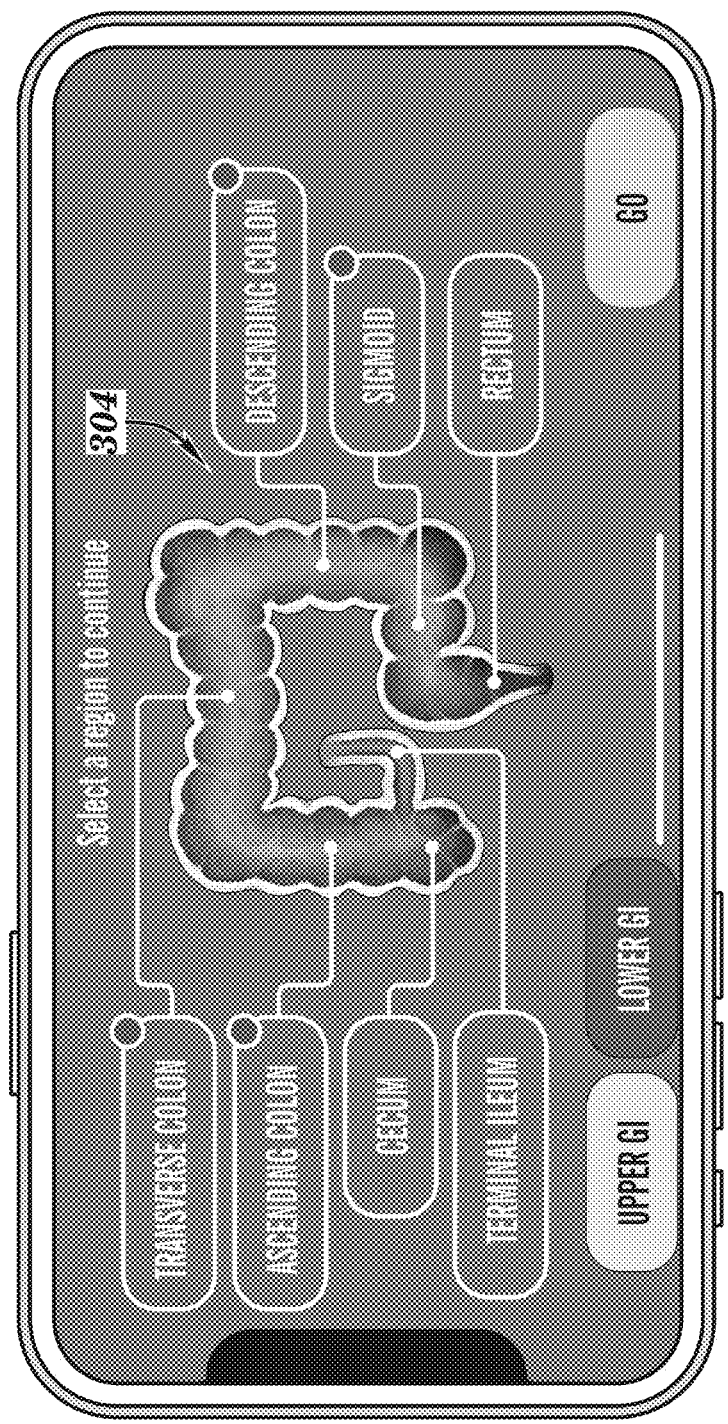
FIG. 11 is a graphical user interface of a further user selection screen for selecting a region of anatomy for a virtual medical tour using a medical report, in accordance with an embodiment of the application.

FIG. 11 depicts a graphical user interface 700 of a further user selection screen for selecting a region of anatomy for a virtual medical tour using a representative medical report, in accordance with an embodiment of the application. In FIG. 11 the user has selected the lower gastrointestinal tract and is preparing to select segments that may disclose conditions of the patient or user. FIG. 11 shows that the lower GI tract has been selected and the user is presented with the following further selections: transverse colon, ascending colon, cecum, terminal ileum, descending colon, sigmoid, and rectum.

Figure 12:
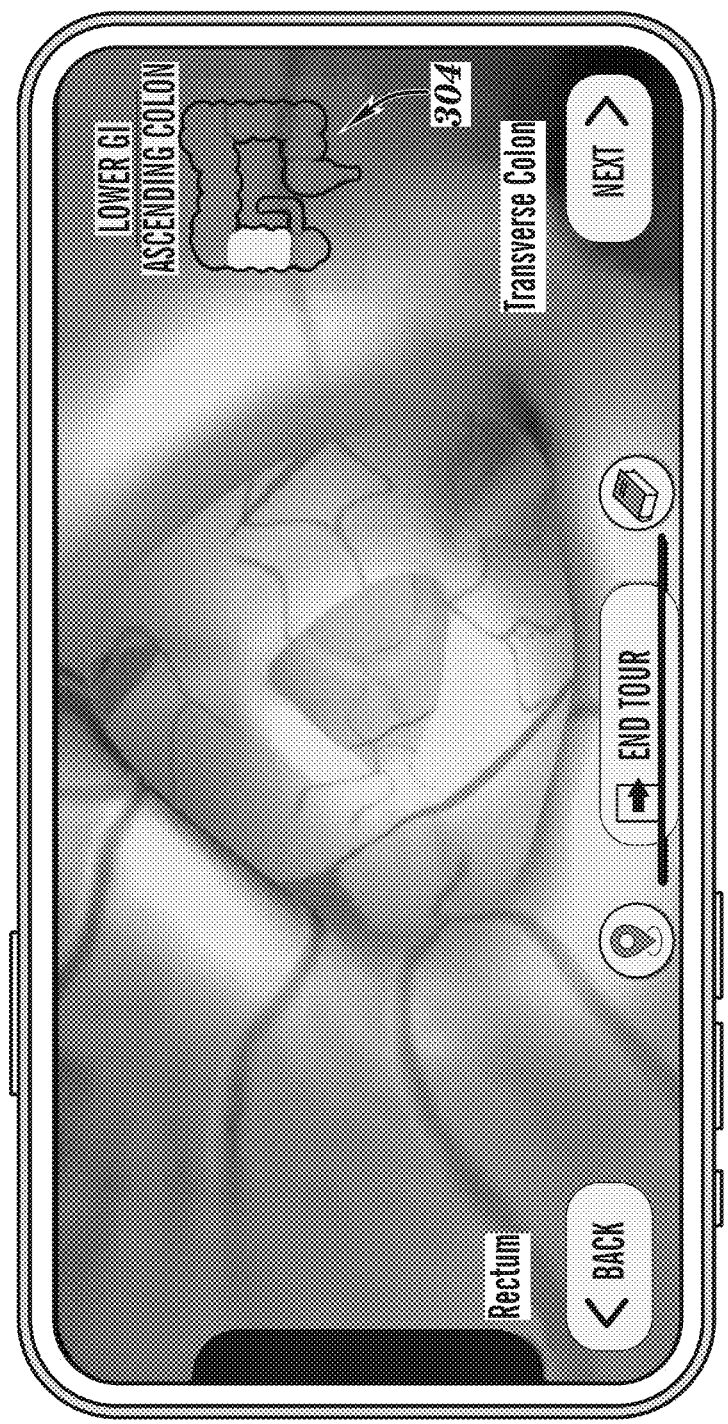
FIG. 12 is a graphical user interface of a further virtual medical tour selected by a user of a medical report, in accordance with an embodiment of the application.

FIG. 12 depicts a graphical user interface 700 of a further virtual medical tour selected by a user of a representative medical report, in accordance with an embodiment of the application. In FIG. 12 a patient or user is viewing the specific area highlighted on the small graphic of the generic diagram 304 displayed on the upper right side of the screen. In some embodiments, the selections made are shown in the generic diagram 304 at the upper right of the screen, with the user having previously selected the lower GI tract and the ascending colon to view on the tour. Navigation buttons allow the user to progress to the next screen, which is the transverse colon, or to the previous screen using the back button, to view the cecum. The use can also navigate and adjust the view utilizing any combination of gestures/motions known in the art, for example, scrolling left or right, pinching inward and outward, etc.

Figure 13:
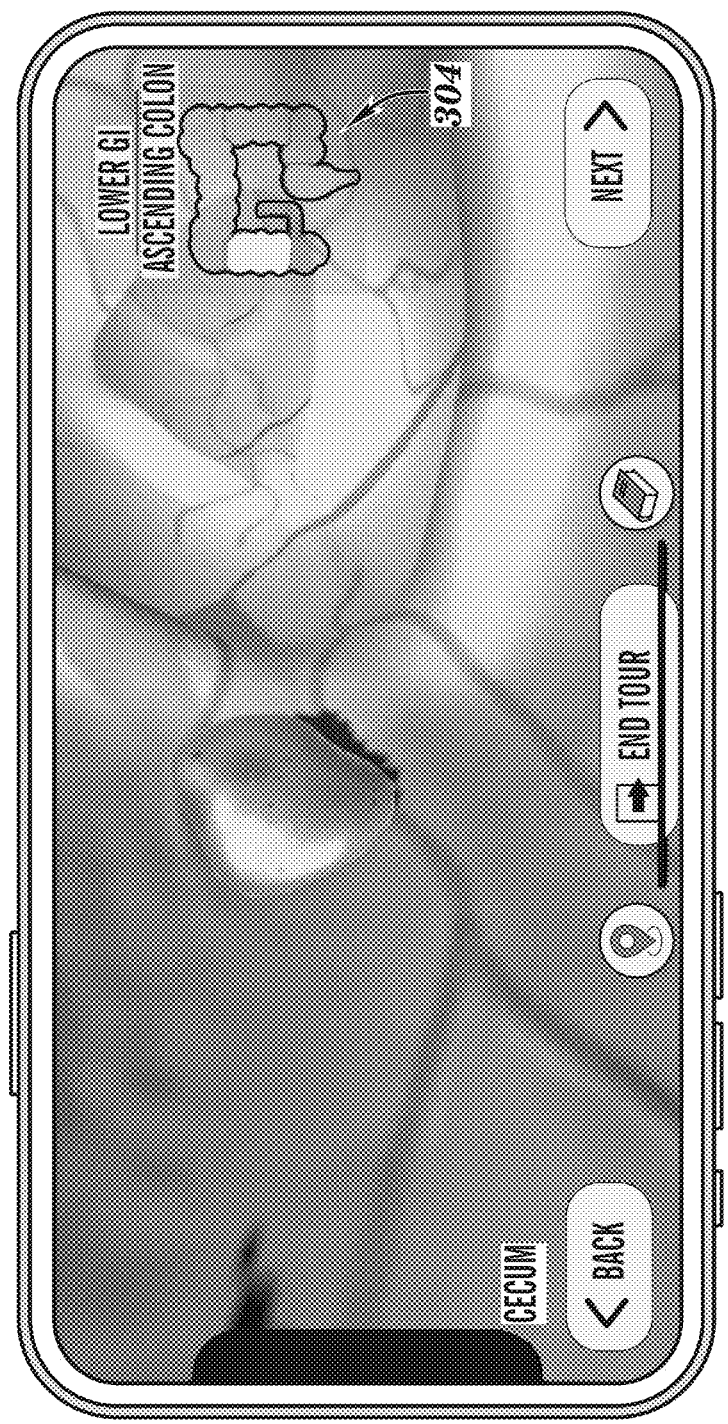
FIG. 13 is a graphical user interface of a finding on the further virtual medical tour of the medical report, in accordance with an embodiment of the application.

FIG. 13 depicts a graphical user interface 700 of a further finding on the virtual medical tour of the representative medical report, in accordance with an embodiment of the application. In FIG. 13 is polyp is clearly visible on the screen, and the upper right of the screen shows the selections of the lower GI tract, and ascending colon, where the polyp may be seen. This location is the location of the polyp within the patient and the tour has been customized by the doctor for the particular patient.

Figure 14:
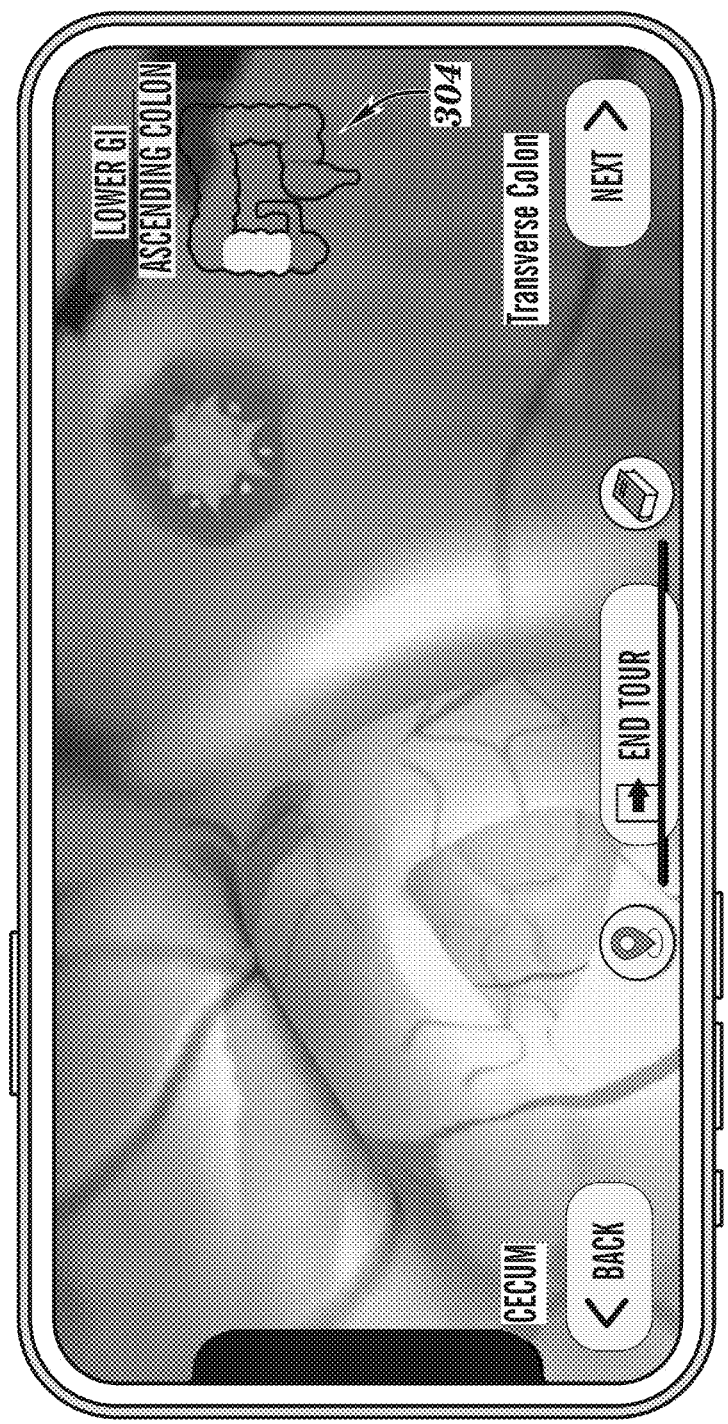
FIG. 14 is a graphical user interface of a further finding in a different anatomical region on the virtual tour of the medical report, in accordance with an embodiment of the application.

FIG. 14 depicts a graphical user interface 700 of a still further finding on the virtual medical tour of the representative medical report, in accordance with an embodiment of the application. In FIG. 14, the user has progressed to the next screen, but continues within the lower GI tract and ascending colon to view further clinical findings.

Figure 15:
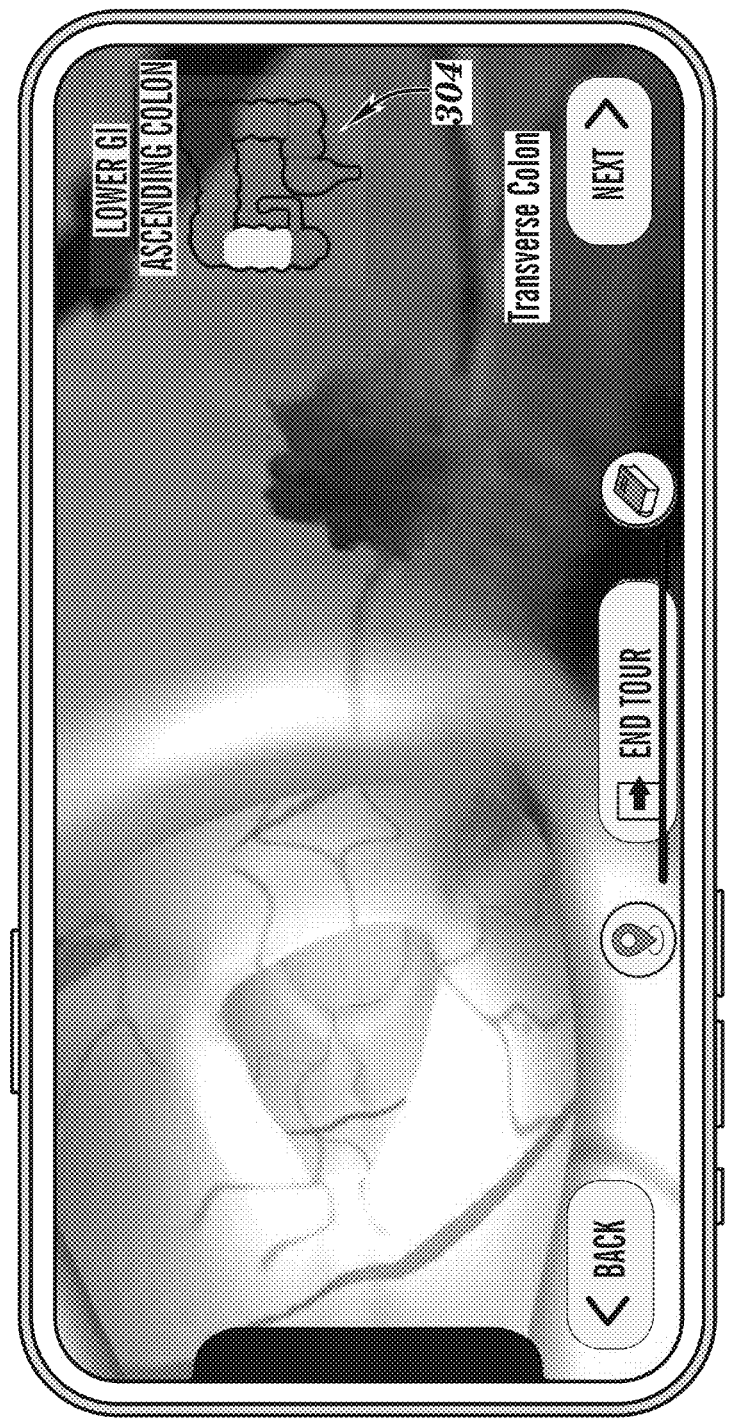
FIG. 15 is a further screen shot of a further finding on the virtual tour of the medical report, in accordance with an embodiment of the application.

FIG. 15 depicts a graphical user interface 700 of a still further finding on the virtual medical tour of the representative medical report, in accordance with an embodiment of the application. In FIG. 15, the user has again progressed, but remains within the lower GI tract and ascending colon.

Figure 16:
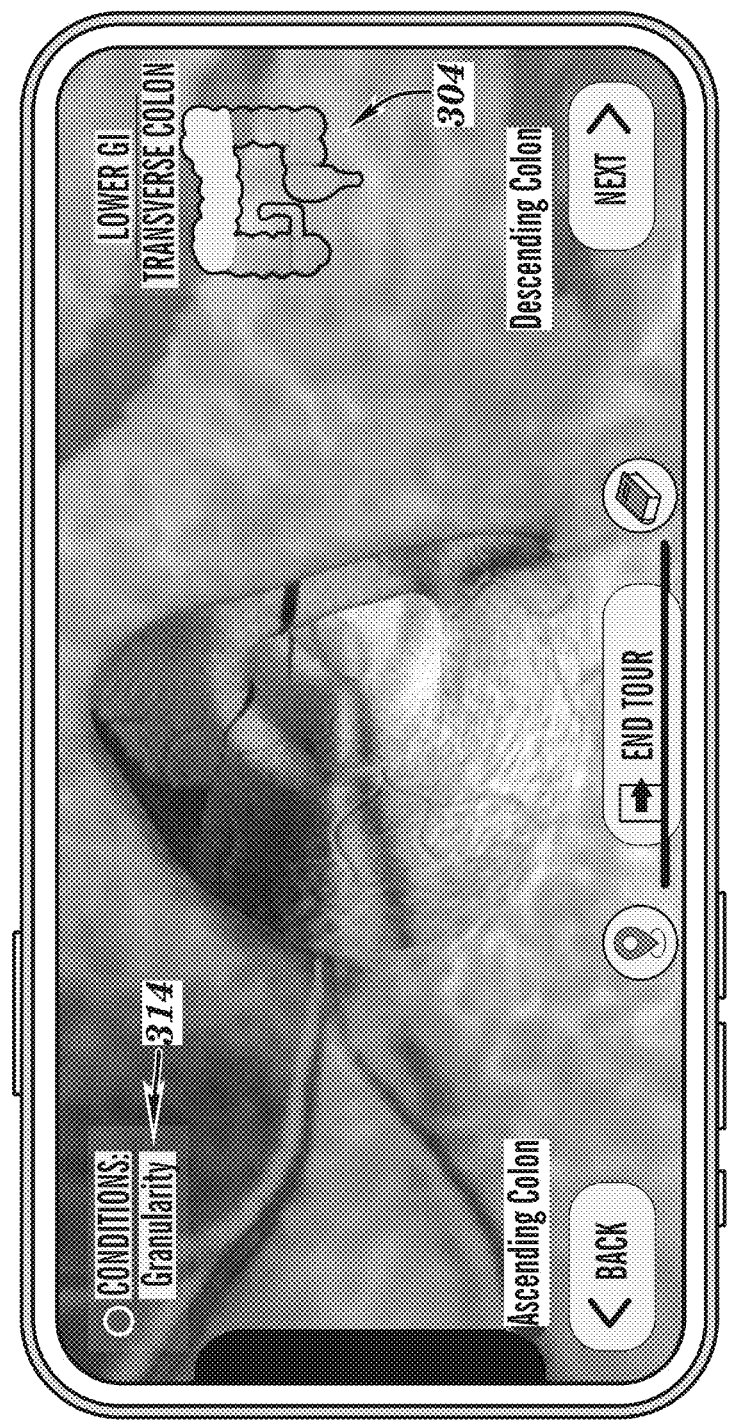
FIG. 16 is a graphical user interface of a further anatomical region on the virtual tour of the medical report, in accordance with an embodiment of the application.

FIG. 16 depicts a graphical user interface 700 of a still further segment on the virtual medical tour of the representative medical report, in accordance with an embodiment of the application. In FIG. 16 the user has moved to the transverse colon, still within the lower GI tract, and is viewing the conditions 314 annotated by a healthcare professional (e.g., during steps discussed in FIGS. 3 and 4) indicated in the upper left corner of the screen, "Conditions." In some embodiments, the user can select the conditions to be provided with additional details providing more information about the conditions being annotated at this location.

Figure 17:
FIG. 17 is a graphical user interface of a still further anatomical region on the virtual tour of the medical report, in accordance with an embodiment of the application.

FIG. 17 depicts a graphical user interface 700 of a diffuse condition 314b on the virtual medical tour of the representative medical report, in accordance with an embodiment of the application. The upper left corner of the screen displays a list of the diffuse conditions 314b shown in patient's view of the screen. In FIG. 17, the user remains in the lower GI and is now viewing a diffuse condition 314b in the terminal ileum.

Figure 18:
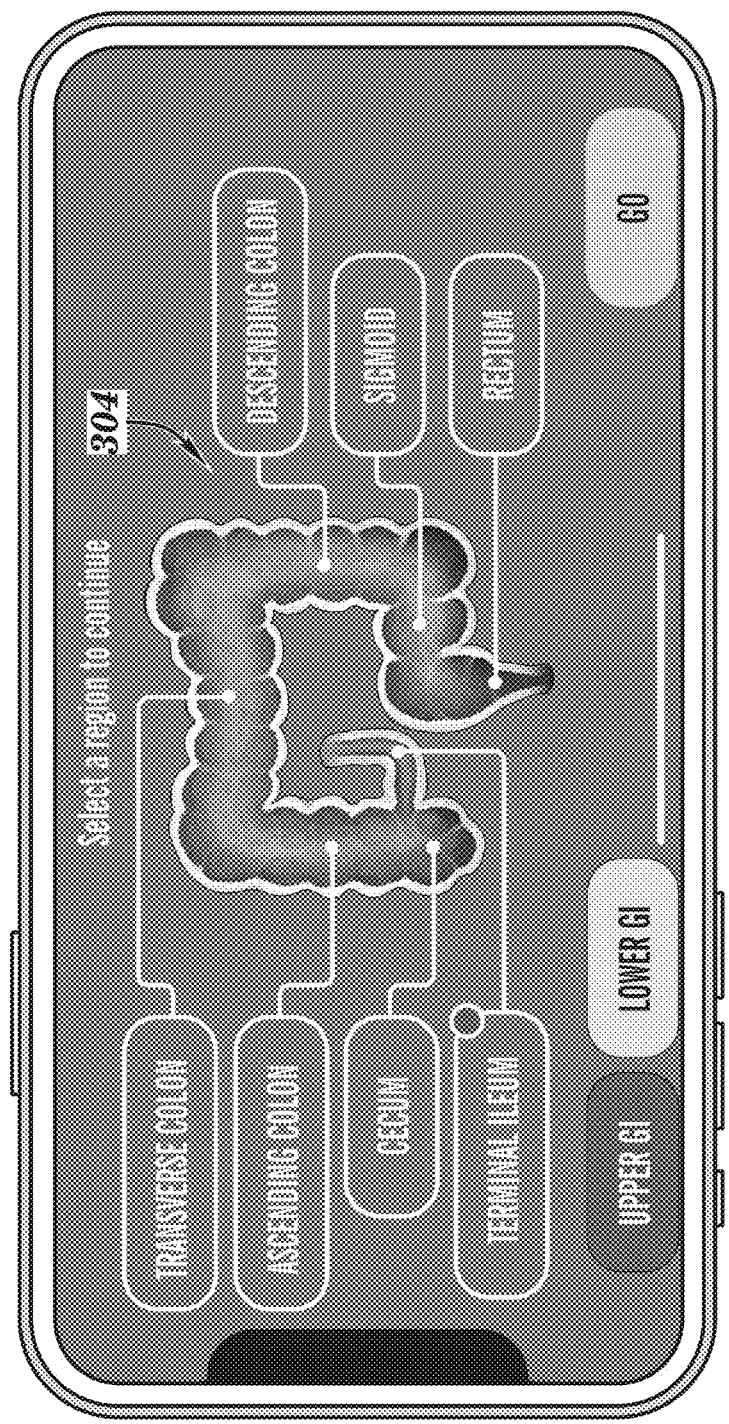
FIG. 18 is screen shot of a region selection screen for a further virtual tour of the medical report, in accordance with an embodiment of the application.

FIG. 18 depicts a graphical user interface 700 of a navigation screen for a user or patient to navigate to another section or segment of the representative medical report, in accordance with an embodiment of the application. FIG. 18 provides a further navigation screen to progress and view different regions, as described above. In some embodiments, the GUI 700 can include circles on the diagram that denote findings and conditions that have been applied to the anatomy (e.g., via drag and drop).

FIG. 19 depicts a table 1900 of selection variables for use by a healthcare professional in preparing a representative medical report for a patient, in accordance with an embodiment of the application. The table shown is used because all of the diffuse conditions 314b, and surgical anastomosis are painted onto the texture and physical geometry, which requires a very large set of maps that need to be applied for each segment. In some embodiments, to determine which maps are to be applied to a specific segment, the output files follow the naming conditions presented in FIG. 19. In some embodiments, the table 1900 can represent how the diffuse condition packages are created and retrieved. As would be appreciated by one skilled in the art, the user does not see this chart, it is generated by the developer and stored for use by the system 100 in the database.

Figure 20:
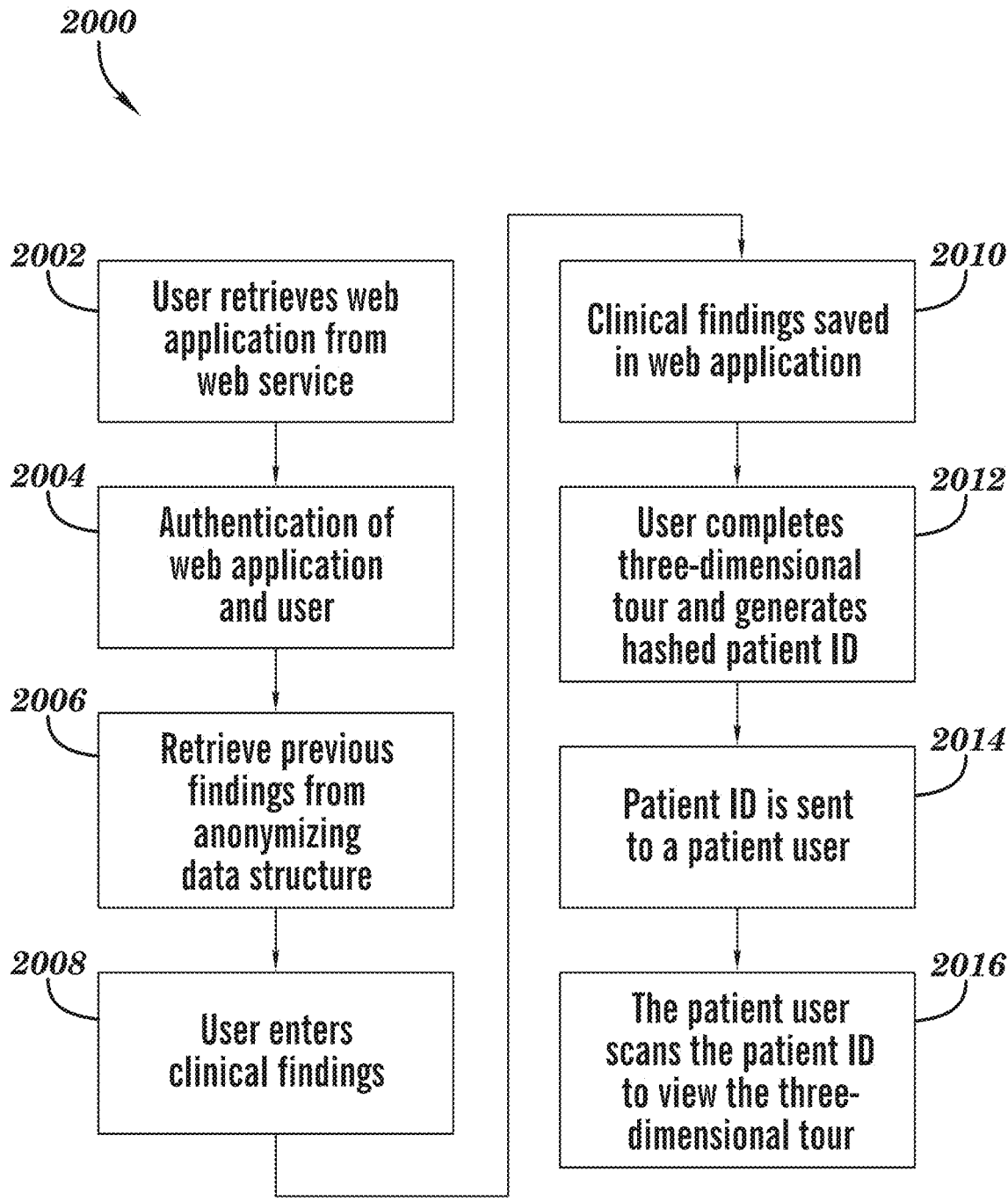
FIG. 20 is a flowchart of a method of creating a medical report for a patient, in accordance with an embodiment of the application.

FIG. 20 depicts a flowchart 200 of a method of creating a representative medical report for a patient, in accordance with an embodiment of the application. The process (2000) begins when a doctor retrieves the web application from the web service in step (2002). The web application and user (doctor) are then authenticated in step (2004). The doctor retrieves the previous findings for the particular patient from the anonymizing data service in step (2006). In step (2008) the doctor enters the clinical findings into the application. In this step the doctor pins specific findings to particular locations on that patient's body or body tract and may also apply diffuse conditions 314b to the patient record being created. In step (2010) the clinical findings are saved in the web application.

In step (2012) the doctor completes the representative medical report when all conditions are placed on the corresponding body segment or part. At this point the doctor generates the QR code that is specific to that patient's virtual tour medical report at that point in time. The virtual tour medical report may be repeated to track changes in the patient's condition and each separate virtual tour medical report will have a unique QR code.

In step (2014) the QR code and any separate medical report, such a PDF of the findings, is sent via email to the patient. The doctor may also provide only the QR code and may present the patient with the physical document during a consultation to review the findings. Once the patient receives the QR code, the patient scans the QR code to take their personalized representative tour of their medical report in step (2016).

Figure 21:
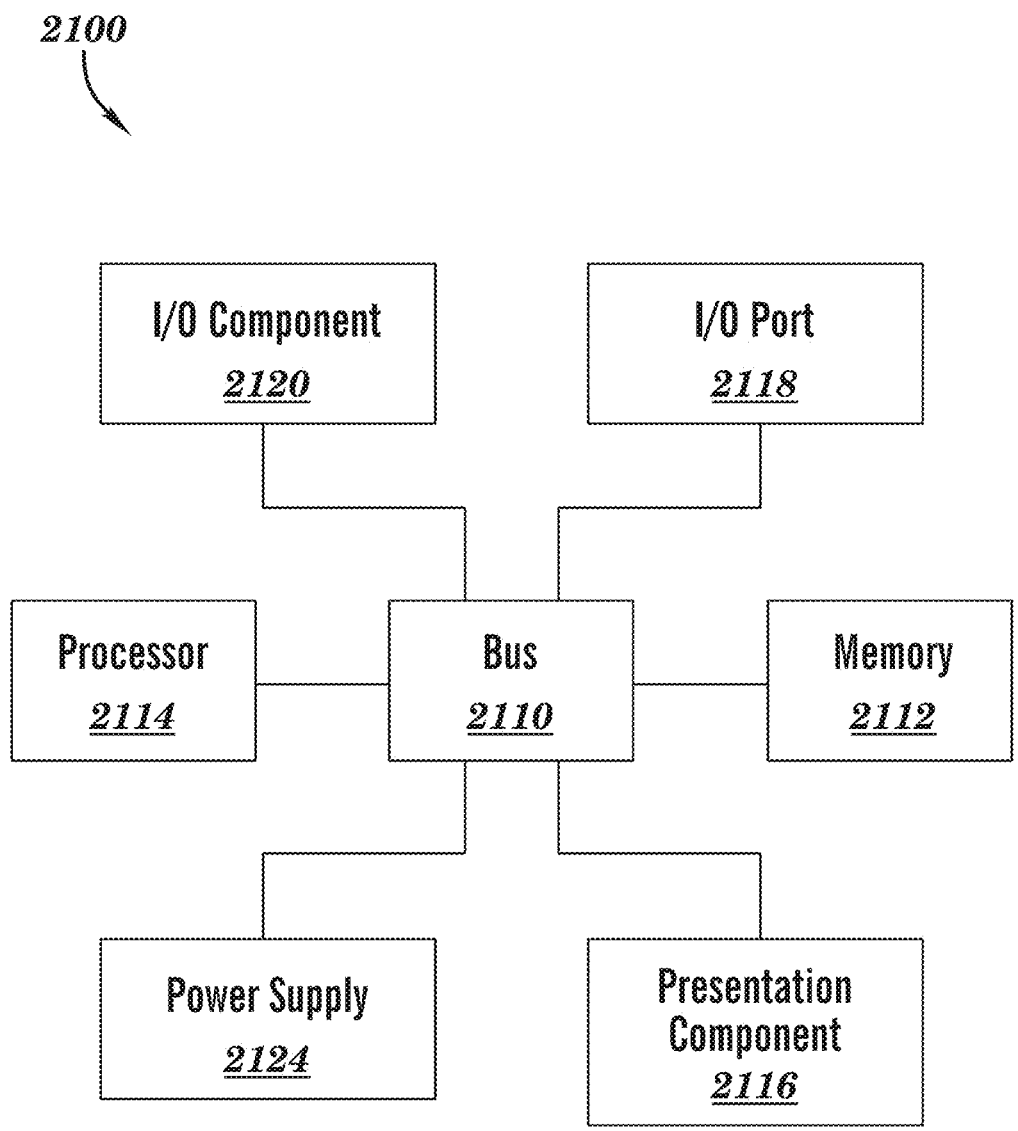
FIG. 21 is an exemplary computer architecture, in accordance with an embodiment of the application.

Any suitable computing device can be used to implement the computing devices 102, 104, 106, 108, 112 and methods/functionality described herein and be converted to a specific system for performing the operations and features described herein through modification of hardware, software, and firmware, in a manner significantly more than mere execution of software on a generic computing device, as would be appreciated by those of skill in the art. One illustrative example of such a computing device 2100 is depicted in FIG. 21. The computing device 2100 is merely an illustrative example of a suitable computing environment and in no way limits the scope of the present invention. A "computing device," as represented by FIG. 21, can include a "workstation," a "server," a "laptop," a "desktop," a "hand-held device," a "mobile device," a "tablet computer," or other computing devices, as would be understood by those of skill in the art. Given that the computing device 2100 is depicted for illustrative purposes, embodiments of the present invention may utilize any number of computing devices 2100 in any number of different ways to implement a single embodiment of the present invention. Accordingly, embodiments of the present invention are not limited to a single computing device 2100, as would be appreciated by one with skill in the art, nor are they limited to a single type of implementation or configuration of the example computing device 2100.

The computing device 2100 can include a bus 2110 that can be coupled to one or more of the following illustrative components, directly or indirectly: a memory 2112, one or more processors 2114, one or more presentation components 2116, input/output ports 2118, input/output components 2120, and a power supply 2124. One of skill in the art will appreciate that the bus 2110 can include one or more busses, such as an address bus, a data bus, or any combination thereof. One of skill in the art additionally will appreciate that, depending on the intended applications and uses of a particular embodiment, multiple of these components can be implemented by a single device. Similarly, in some instances, a single component can be implemented by multiple devices. As such, FIG. 21 is merely illustrative of an exemplary computing device that can be used to implement one or more embodiments of the present invention, and in no way limits the invention.

The computing device 2100 can include or interact with a variety of computer-readable media. For example, computer-readable media can include Random Access Memory (RAM); Read Only Memory (ROM); Electronically Erasable Programmable Read Only Memory (EEPROM); flash memory or other memory technologies; CD-ROM, digital versatile disks (DVD) or other optical or holographic media; magnetic cassettes, magnetic tape, magnetic disk storage or other magnetic storage devices that can be used to encode information and can be accessed by the computing device 2100.

The memory 2112 can include computer-storage media in the form of volatile and/or nonvolatile memory. The memory 2112 may be removable, non-removable, or any combination thereof. Exemplary hardware devices are devices such as hard drives, solid-state memory, optical-disc drives, and the like. The computing device 2100 can include one or more processors that read data from components such as the memory 2112, the various I/O components 2116, etc. Presentation component(s) 2116 present data indications to a user or other device. Exemplary presentation components include a display device, speaker, printing component, vibrating component, etc.

The I/O ports 2118 can enable the computing device 2100 to be logically coupled to other devices, such as I/O components 2120. Some of the I/O components 2120 can be built into the computing device 2100. Examples of such I/O components 2120 include a microphone, joystick, recording device, game pad, satellite dish, scanner, printer, wireless device, networking device, and the like.

The described embodiments are to be considered in all respects only as illustrative and not restrictive and the scope of the presently disclosed embodiments is, therefore, indicated by the appended claims rather than by the foregoing description. All changes which come within the meaning and range of equivalency of the claims are to be embraced within their scope. Skilled artisans may implement the described functionality in varying ways for each particular application, but such implementation decisions should not be interpreted as causing a departure from the scope of the disclosed apparatus and/or methods.

What is claimed is:

1. A computer-implemented method for creating a representative tour medical report, the method comprising:
   receiving an electronic medical record comprising medical findings from a procedure for a specific patient from a medical records server;
   receiving medical imaging data corresponding to a body part or tract associated with the medical findings from a medical records server;
   outputting, at an output device of a healthcare provider device, a virtual reality visualization screen for the body part or tract comprising a plurality of interface elements within an outline of the body part or tract, the outline of the body part or tract comprising a plurality of peg elements in the plurality of interface elements;
   receiving, at a user input device of the healthcare provider device, one or more selections of the plurality of peg elements for configuring the representative tour medical report, the one or more selections mapping the medical findings to one or more selected peg elements in the plurality of peg elements, wherein a particular medical finding is mapped to a particular selected peg element by a user positioning an icon representing a condition associated with the particular medical finding onto the particular selected peg element, wherein each peg element may only contain one condition and if the user attempts to position the icon onto a peg element that is already occupied, the icon being positioned is prevented from being placed onto the peg element that is already occupied;
   determining the one or more conditions associated with the medical findings mapped to the one or more selected peg elements of the plurality of peg elements;
   generating the representative tour medical report by:
      generating one or more denoted locations in the medical imaging data correlated to the one or more selected peg elements based on the medical findings associated with the medical imaging data;
      generating a three-dimensional visual representation of an anatomy associated with the body part or tract, the three-dimensional visual representation comprising a geometry based at least on the medical imaging data and the one or more selected peg elements;
      generating one or more denoted condition segments within the three-dimensional visual representation by painting a texture onto the geometry at the one or more denoted locations based on the one or more conditions;
      generating a two-dimensional overlay of the three-dimensional visual representation of the anatomy, the overlay comprising at least one selected from the group of:
         one or more annotations of the medical findings; and
         the outline of the body part or tract;
   storing, upon the configuring, the representative tour medical report linked to a patient identifier (ID) of the specific patient; and
   generating a computer-readable access code encoding the patient ID configured to enable the specific patient, upon scanning the computer-readable access code, to access and view the representative tour medical report.

2. The method of claim 1, wherein receiving the one or more selections of the plurality of peg elements for the body part or tract comprises receiving localized medical findings pinned to a designated peg element of the plurality of peg elements in the virtual reality visualization screen.

3. The method of claim 2, wherein the localized medical findings are locations on a specific patient and relate to at least one of: gastrointestinal tract, cardiac system, vascular system, oral, and esophageal systems.

4. The method of claim 1, wherein determining the one or more conditions associated with the medical findings mapped to the one or more selected peg elements comprises determining one or more diffuse medical findings associated with the one or more selected peg elements.

5. The method of claim 1, further comprising: receiving one or more sub-segment selections of the plurality of interface elements for a sub-segment of the patient's body tract;
   wherein the received one or more sub-segment selections comprises entering findings for at least one of the following sub-segments: esophagus, stomach, duodenum, upper GI, lower GI, transverse colon, ascending colon, cecum, terminal ileum, descending colon, sigmoid, and rectum.

6. The method of claim 5, wherein both the upper GI and lower GI tract are composed of multiple sub-segments.

7. The method of claim 6, wherein each of the multiple sub-segments that forms a representation of the patient's GI tract has localized conditions and diffuse conditions.

8. The method of claim 7, wherein the method of creating the representative tour medical report is repeated for multiple sub-segments of the patient's GI tract, forming an end-to-end tract of the patient's GI tract.

9. The method of claim 1, further comprising: sending the computer-readable access code for the representative tour medical report to the specific patient.

10. The method of claim 1, further comprising: providing the specific patient with a choice to view a generic virtual medical tour related to a medical condition of the specific patient or to view the representative tour medical report customized for the specific patient.

11. The method of claim 1, further comprising: providing the representative tour medical report as a virtual reality visualization medical tour.

12. The method of claim 11, wherein the virtual reality visualization medical tour comprises at least one clinical finding of a procedure or a scan image of a patient.

13. The method of claim 11, where the virtual reality visualization medical tour is constructed for successive procedures of a same type.

14. The method of claim 11, further comprising: providing a 2D or 3D virtual rendering of the virtual reality visualization medical tour, in addition to a virtual reality headset.

15. The method of claim 1, wherein receiving the medical imaging data comprises receiving real-world images or videos taken during the procedure.

16. A non-transitory computer-readable medium containing instructions, which when executed cause a processor to perform the following steps:
receiving an electronic medical record comprising medical findings from a procedure for a specific patient from a medical records server;
receiving medical imaging data corresponding to a body part or tract associated with the medical findings from a medical records server;
outputting, at an output device of a healthcare provider device, a virtual reality visualization screen for a body part or tract comprising a plurality of interface elements within the outline of the body part or tract, the outline of the body part or tract comprising a plurality of peg elements in the plurality of interface elements;
receiving, at a user input device of the healthcare provider device, one or more selections of the plurality of peg elements for configuring the representative tour medical report, the one or more selections mapping the medical findings to one or more selected peg elements in the plurality of peg elements, wherein a particular medical finding is mapped to a particular selected peg element by a user positioning an icon representing a condition associated with the particular medical finding onto the particular selected peg element, wherein each peg element may only contain one condition and if the user attempts to position the icon onto a peg element that is already occupied, the icon being positioned is prevented from being placed onto the peg element that is already occupied;
determining the one or more conditions associated with the medical findings mapped to the one or more selected peg elements of the plurality of peg elements;
generating the representative tour medical report by:
generating one or more denoted locations in the medical imaging data correlated to the one or more selected peg elements based on the medical findings associated with the medical imaging data;
generating a three-dimensional visual representation of an anatomy associated with the body part or tract, the three-dimensional visual representation comprising a geometry based at least on the medical imaging data and the one or more selected peg elements;
generating one or more denoted condition segments within the three-dimensional visual representation by painting a texture onto the geometry at the one or more denoted locations based on the one or more conditions;
generating a two-dimensional overlay of the three-dimensional visual representation of the anatomy, the overlay comprising at least one selected from the group of:
one or more annotations of the medical findings; and
the outline of the body part or tract;
storing, upon the configuring, the representative tour medical report linked to a patient identifier (ID) of the specific patient; and
generating a computer-readable access code encoding the patient ID configured to enable the specific patient, upon scanning the computer-readable access code, to access and view the representative tour medical report.

17. The non-transitory computer-readable medium of claim 16, further comprising instructions for:
receiving the one or more selections of the plurality of peg elements for the body part or tract comprising receiving localized medical findings pinned to a designated peg element of the plurality of peg elements in the virtual reality visualization screen, wherein the body part or tract is a gastrointestinal (GI) tract.

18. The non-transitory computer-readable medium of claim 17, further comprising instructions for:
determining the one or more conditions associated with the medical findings mapped to the one or more selected peg elements comprising determining one or more diffuse medical findings associated with a selected segment of the GI tract.

19. The non-transitory computer-readable medium of claim 16, further comprising instructions for: receiving one or more sub-segment selections of the plurality of interface elements for a sub-segment of the patient's body tract;
wherein the received one or more sub-segment selections comprises entering findings for at least one of the following sub-segments of the tract: esophagus, stomach, duodenum, upper GI, lower GI, transverse colon, ascending colon, cecum, terminal ileum, descending colon, sigmoid, and rectum.

* * * * *